United States Patent
Hu et al.

(10) Patent No.: US 12,234,239 B2
(45) Date of Patent: Feb. 25, 2025

(54) CRYSTALLINE FORMS OF 2-(3-(4-(7H-PYRROLO[2,3-D]PYRIMIDIN-4-YL)-1H-PYRAZOL-1-YL)-1-(CYCLOPROPYLSULFONYL)AZETIDIN-3-YL)ACETONITRILE

(71) Applicant: Elanco US, Inc., Greenfield, IN (US)

(72) Inventors: Jingdan Hu, Greenfield, IN (US); Timothy Andrew Woods, Greenfield, IN (US)

(73) Assignee: Elanco US Inc., Greenfield, IN (US)

( * ) Notice: Subject to any disclaimer, the term of this patent is extended or adjusted under 35 U.S.C. 154(b) by 0 days.

(21) Appl. No.: 17/830,898

(22) Filed: Jun. 2, 2022

(65) Prior Publication Data

US 2023/0056365 A1    Feb. 23, 2023

Related U.S. Application Data

(62) Division of application No. 16/855,471, filed on Apr. 22, 2020, now Pat. No. 11,548,895.

(60) Provisional application No. 62/837,972, filed on Apr. 24, 2019.

(51) Int. Cl.
| | |
|---|---|
| *A61K 31/519* | (2006.01) |
| *A61P 17/00* | (2006.01) |
| *A61P 37/08* | (2006.01) |
| *C07D 487/04* | (2006.01) |

(52) U.S. Cl.
CPC ............ *C07D 487/04* (2013.01); *A61P 17/00* (2018.01); *A61P 37/08* (2018.01); *C07B 2200/13* (2013.01)

(58) Field of Classification Search
CPC ............................. A61K 31/519; C07D 487/04
USPC ........................................ 514/265.1; 544/280
See application file for complete search history.

(56) References Cited

U.S. PATENT DOCUMENTS

| | | | |
|---|---|---|---|
| 2018/0044342 A1 | 2/2018 | Chen et al. | |
| 2020/0339585 A1 | 10/2020 | Hu | |

FOREIGN PATENT DOCUMENTS

| | | |
|---|---|---|
| CN | 102026999 B | 4/2011 |
| JP | 2011514909 A | 5/2011 |
| JP | 2011-514909 | 8/2013 |
| WO | 2007070514 A1 | 6/2007 |
| WO | 2007070589 | 6/2007 |
| WO | 2009114512 A1 | 9/2009 |
| WO | 2013173506 A2 | 11/2013 |
| WO | 2016141891 A1 | 9/2016 |
| WO | 2016205487 A1 | 12/2016 |
| WO | 2019003249 A1 | 1/2019 |
| WO | 2020219524 A1 | 10/2020 |

OTHER PUBLICATIONS

Office Action issued in corresponding Korean Application No. 10-2021-7033869 (Jan. 9, 2024).
Hillier A, Griffin CE (2001). The ACVD task force on canine atopic dermatitis (I) incidence and prevalence. Vet Immunol Immunopathol; 81:147-151.
Renauld J-C (2003). Class II cytokine receptors and their ligands: key antiviral and inflammatory modulators. Nat Rev Immunol. 3: 667-76.
Rybníçek J_et al. (2009). Further validation of a pruritus severity scale for use in dogs. VetDermatol 20: 115-122.
Gonzales AJ et.al. (2013). Interleukin-31: Its Role in Canine Pruritus and Naturally Occurring Canine Atopic Dermatitis. Vet Dermatol 24(1): 48-53 e11-2.
Cosgrove, S. B. et al (2013). Efficacy and safety of oclacitinib for the control of pruritus and associated skin lesions in dogs with canine allergic dermatitis. Vet Dermatol 5(4):479-e114.
Thierry Olivry et.al. (2014). Validation of the Canine Atopic Dermatitis Extent and Severity Index (CADESI)-4, a simplified severity scale for assessing skin lesions of atopic dermatitis in dogs. Vet Dermatol 25: 77-e25.
Christian Reichard. Solvents and Media Effects in Organic Chemistry. Publishing House Mir, 1991, 763 p (pp. 611-614, section A5).
Caira Topics in Current Chemistry (1998) 198 pp. 163-208.
Rodriguez-Spong et al. Advanced Drug Delivery Reviews (2004) 56: 241-274.
Lv Yang et al. People's Health Publishing House "Polymorphic Drugs" (2009).

(Continued)

*Primary Examiner* — Douglas M Willis
(74) *Attorney, Agent, or Firm* — McBee Moore & Vanik IP, LLC

(57) ABSTRACT

The present disclosure provides crystalline forms of 2-(3-(4-(7H-pyrrolo[2,3-d]pyrimidin-4-yl)-1H-pyrazol-1-yl)-1-(cyclopropylsulfonyl)azetidin-3-yl)acetonitrile, pharmaceutical compositions comprising the crystalline forms, methods of using the crystalline forms, and processes for making the crystalline forms.

33 Claims, No Drawings

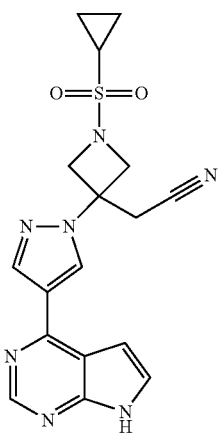

(I)

(56) References Cited

OTHER PUBLICATIONS

Byrn et al., "Pharmaceutical Solids: A Strategic Approach to Regulatory Considerations", Pharmaceutical Research, 1995, vol. 12, No. 7, pp. 945-954.
Mitsuhisa Yamano, "Approach to crystal polymorphism in pharmaceutical process research", Journal of the Society of Organic Synthetic Chemistry, Sep. 1, 2007, vol. 65, No. 9, pp. 907-913.
Noriyuki Takada, "Drug Form Screening and Selection at the Drug Discovery Stage", Pharm Stage, Jan. 15, 2007, vol. 6, No. 10, pp. 20-25.
Hiroshi Oshima, "Precipitation behavior and control of crystal polymorphs and pseudopolymorphs", Pharm Stage, Jan. 15, 2007, vol. 6, No. 10, pp. 48-53.
Yoko Kawaguchi et al., "Pharmaceuticals and crystal polymorphisms", Biotechnology Research, 2002, vol. 4, No. 2, pp. 310-317.
Sarma B. et al. Solid formation of pharmaceuticals: Polymorphs, salt and cocrystals. Korean J.Chem.Eng., 2011, 28 (2), p. 315-322. Abstract only.
Williams et al., "Content Uniformity and Dose Uniformity: Current Approaches, Statistical Analyses, and Presentation pf an Alternative Approach, with Special Reference to Oral Inhalation and Nasal Drug Products," Pharmaceutical Research, Apr. 1, 2002, pp. 359-366.
Anonymous, "Uniformity of Dosage Units 1," USP—Stage 6 Harmonization, Jan. 1, 2011, XP05588725, pp. 1-3. Retrieved from the internet on Feb. 3, 2022: <https://www.usp.org/sites/default/files/usp/document/riarmonization/gen-method/q0304_stage_6_monograph_25_feb_2011.pdf>.

CRYSTALLINE FORMS OF 2-(3-(4-(7H-PYRROLO[2,3-D]PYRIMIDIN-4-YL)-1H-PYRAZOL-1-YL)-1-(CYCLOPROPYLSULFONYL) AZETIDIN-3-YL)ACETONITRILE

CROSS-REFERENCE TO RELATED APPLICATIONS

This application is a division of U.S. application Ser. No. 16/855,471, filed 22 Apr. 2020, which claims priority to U.S. Provisional Application 62/837,972, filed 24 Apr. 2019, the contents of which are herein incorporated by reference in their entirety.

TECHNICAL FIELD

The present disclosure relates to polymorphs of 2-(3-(4-(7H-pyrrolo[2,3-d]pyrimidin-4-yl)-1H-pyrazol-1-yl)-1-(cyclopropylsulfonyl)azetidin-3-yl)acetonitrile, to pharmaceutical compositions and processes for preparing the same, and to methods of using the same, for example, for the treatment of dermatological conditions.

BACKGROUND

International Application Publication WO/2009/114512 discloses certain JAK inhibitors, including the compound 2-(3-(4-(7H-pyrrolo[2,3-d]pyrimidin-4-yl)-1H-pyrazol-1-yl)-1-(cyclopropylsulfonyl)azetidin-3-yl)acetonitrile (Example 80), its preparation as a trifluoroacetic acid salt (Example 2), and as a phosphoric acid salt (Example 81).

Summary

There is a need for 2-(3-(4-(7H-pyrrolo[2,3-d]pyrimidin-4-yl)-1H-pyrazol-1-yl)-1-(cyclopropylsulfonyl)azetidin-3-yl)acetonitrile which can be effectively, safely, and reproducible used, and for methods for preparation and purification which can be used efficiently and reproducibly on a large scale for industrial manufacture. In particular, there is a need for crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile which can be effectively, safely, and reproducible used, and for methods for preparation and purification which can be used efficiently and reproducibly on a large scale for industrial manufacture. More particularly, there is a need for substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile which can be effectively, safely, and reproducible used, and for methods for preparation and purification which can be used efficiently and reproducibly on a large scale for industrial manufacture.

In certain embodiments, the present disclosure provides a substantially polymorphically pure crystalline form I 2-(3-(4-(7H-pyrrolo[2,3-d]pyrimidin-4-yl)-1H-pyrazol-1-yl)-1-(cyclopropylsulfonyl)azetidin-3-yl)acetonitrile and processes for making the same. In certain embodiments, the present disclosure provides a substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile and processes for making the same. In certain embodiments, the present disclosure provides a substantially polymorphically pure form III 2-(3-(4-(7H-pyrrolo[2,3-d]pyrimidin-4-yl)-1H-pyrazol-1-yl)-1-(cyclopropylsulfonyl)azetidin-3-yl)acetonitrile and processes for making the same.

In certain embodiments, the present disclosure provides a pharmaceutical composition comprising a substantially polymorphically pure form I 2-(3-(4-(7H-pyrrolo[2,3-d]pyrimidin-4-yl)-1H-pyrazol-1-yl)-1-(cyclopropylsulfonyl)azetidin-3-yl)acetonitrile and a pharmaceutically acceptable excipient. In certain embodiments, the present disclosure provides a pharmaceutical composition comprising a substantially polymorphically pure form II 2-(3-(4-(7H-pyrrolo[2,3-d]pyrimidin-4-yl)-1H-pyrazol-1-yl)-1-(cyclopropylsulfonyl)azetidin-3-yl)acetonitrile and a pharmaceutically acceptable excipient. In certain embodiments, the present disclosure provides a pharmaceutical composition comprising a substantially polymorphically pure form III 2-(3-(4-(7H-pyrrolo[2,3-d]pyrimidin-4-yl)-1H-pyrazol-1-yl)-1-(cyclopropylsulfonyl)azetidin-3-yl)acetonitrile and a pharmaceutically acceptable excipient.

In certain embodiments, the present disclosure provides a method of treating a dermatological condition comprising administering to a non-human mammal in need thereof an effective amount of the substantially polymorphically pure form I 2-(3-(4-(7H-pyrrolo[2,3-d]pyrimidin-4-yl)-1H-pyrazol-1-yl)-1-(cyclopropylsulfonyl)azetidin-3-yl)acetonitrile.

In certain embodiments, the present disclosure provides a method of treating a dermatological condition comprising administering to a non-human mammal in need thereof an effective amount of the substantially polymorphically pure form II 2-(3-(4-(7H-pyrrolo[2,3-d]pyrimidin-4-yl)-1H-pyrazol-1-yl)-1-(cyclopropylsulfonyl)azetidin-3-yl)acetonitrile.

In certain embodiments, the present disclosure provides a method of treating a dermatological condition comprising administering to a non-human mammal in need thereof an effective amount of the substantially polymorphically pure form III 2-(3-(4-(7H-pyrrolo[2,3-d]pyrimidin-4-yl)-1H-pyrazol-1-yl)-1-(cyclopropylsulfonyl)azetidin-3-yl)acetonitrile.

In certain embodiments, the present disclosure provides a process for making 2-(3-(4-(7H-pyrrolo[2,3-d]pyrimidin-4-yl)-1H-pyrazol-1-yl)-1(cyclopropylsulfonyl)azetidin-3-yl)acetonitrile and intermediates thereof.

DETAILED DESCRIPTION

The present disclosure relates to a compound, 2-(3-(4-(7H-pyrrolo[2,3-d]pyrimidin-4-yl)-1H-pyrazol-1-yl)-1-(cyclopropylsulfonyl)azetidin-3-yl)acetonitrile, polymorphs thereof identified herein as form I, form II, and form III and pharmaceutical compositions thereof and methods of using the polymorphs, for example, for the treatment of dermatological conditions, methods of making the polymorphs, and methods of making the compound and intermediates thereof.

1. DEFINITIONS

Unless otherwise defined, all technical and scientific terms used herein have the same meaning as commonly understood by one of ordinary skill in the art. In case of conflict, the present document, including definitions will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The term "about" when used in connection with a measurable numerical variable, refers to the indicated value of the variable and to all values of the variable that are within the experimental error of the indicated value or within ±10 percent of the indicated value, whichever is greater.

The term "acceptable excipient" refers to those typically used in preparing veterinary and pharmaceutical compositions and should be pure and non-toxic in the amounts used. They generally are a solid, semi-solid, or liquid material which in the aggregate can serve as a vehicle or medium for the active ingredient. Some examples of acceptable excipients are found in Remington's Pharmaceutical Sciences and the Handbook of Pharmaceutical Excipients and include diluents, vehicles, carriers, ointment bases, binders, disintegrates, lubricants, glidants, sweetening agents, flavoring agents, gel bases, sustained release matrices, stabilizing agents, preservatives, solvents, suspending agents, buffers, emulsifiers, dyes, propellants, coating agents, and others.

The term "aromatic solvent" refers to a benzene optionally substituted with one or two substituents selected from the group consisting of methyl, chloro, bromo, cyano, nitro, aceto. The term "aromatic solvent" specifically includes, nitrobenzene, chlorobenzene, toluene, xylene, and acteophenone.

The term "$C_{1-5}$ alcohol" refers to a straight or branched alkanol having from one to five carbon atoms, for example methanol, ethanol, n-propanol, iso-propanol, 1-butanol, ethylene glycol, 1,3-propanediol, and the like.

The term "$C_1$-$C_4$ alkyl" refers to a straight or branched alkyl chain having from one to four carbon atoms and includes methyl, ethyl, propyl, isopropyl, butyl, and the like.

The term "$C_{2-8}$ alkyl ether" refers to a straight, branched, or cyclic alkyl ether having a total of from two to eight carbon atoms, for example dimethyl ether, diethyl ether, methyl t-butyl ether, THF, 2-methyl THF, dioxane, and the like.

The term "$C_{3-8}$ alkyl acetate" refers to straight or branched alkyl esters of acetic acid having a total of three to eight carbons, for example, methyl acetate, ethyl acetate, isopropyl acetate, butyl acetate, isobutyl acetate, and the like.

The term "$C_{2-5}$ alkyl cyanide" refers to straight or branched alkyl cyanides having a total of two to five carbon atoms, for example acetonitrile, proprionitrile, and butyronitrile.

The term "$C_{3-9}$ alkyl ketone" refers to a straight, branched, or cyclic alkyl group having an oxo group and having a total of from three to nine carbon atoms, for example acetone, methyl ethyl ketone, and cyclohexanone.

The term "$C_{5-8}$ hydrocarbon" refers to a straight, branched, or cyclic saturated alkyl hydrocarbon, for example, pentane, hexane, heptane, octane, cyclopentane, cyclohexane, methyl cyclohexane and the like.

The term "5-6 membered heterocyclic ring" refers to a 5 to 6 membered monocyclic saturated ring that includes the oxygen atoms to which $R_1$ and $R_2$ are attached and boron to which those oxygen atoms are attached.

The terms "crystallize," "crystallizing," "crystallization," and the like refer to complete dissolution followed by precipitation and slurry processes that do not involve complete dissolution. Slurry processes include those that encompass continuation of the crystallization process following precipitation after complete dissolution.

The term "dermatological conditions" includes skin disorders such as psoriasis (for example, psoriasis vulgaris), atopic dermatitis, skin rash, skin irritation, skin sensitization (e.g., contact dermatitis or allergic contact dermatitis), pruritus, including pruritus associated with allergic dermatitis, and allergic reactions.

The term "effective amount" refers to the amount or dose of compound of the invention, or a pharmaceutically acceptable salt thereof which, upon single or multiple dose administration to the patient, provides the desired effect in the patient under diagnosis or treatment. An effective amount can be readily determined by the attending diagnostician, as one skilled in the art, by the use of known techniques and by observing results obtained under analogous circumstances. In determining the effective amount for a patient, a number of factors are considered by the attending diagnostician, including, but not limited to: the species of patient or non-human mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

The terms "patient," "subject," and "non-human mammal" refers to a warm blooded animal, such as dogs, cats, mice, rats, guinea pigs, rabbits, cows, horses, sheep, goats, and pigs. Particular non-human mammals are pets or companion animals, such as dogs and cats and also mice, guinea pigs, and rabbits. Preferred non-human mammals are dogs and cats. Preferably, the non-human mammal is a canine. A particularly preferred non-human mammal is the dog.

The term "salt" refers to salts of veterinarily or pharmaceutically acceptable organic acids and bases or inorganic acids and bases. Such salts are well known in the art and include those described in Journal of Pharmaceutical Science, 66, 2-19 (1977). An example is the hydrochloride salt. The term as used herein expressly excludes a trifluoroacetic acid salt and a phosphoric acid salt.

The term "substantially polymorphically pure" refers to greater than 90%, preferably greater than 97%, more preferably greater than 99%, and even more preferably greater than 99.5% polymorphic purity.

The terms "treating" or "to treat" refer to restraining, slowing, stopping, or reversing the progression or severity of an existing symptom or disorder.

The term "water activity" is equal to p/p* where p is the partial vapor pressure of water in the solution, and p* is the partial vapor pressure of pure water at the same temperature.

For the recitation of numeric ranges herein, each intervening number there between with the same degree of precision is explicitly contemplated. For example, for the range of 92-97, the numbers 93, 94, 95, and 96 are contemplated in addition to 92 and 97, and the number 92.1, 92.2, 92.3, 92.4, 92.5, 92.6 et cetera to 97.0 are explicitly contemplated to be within the range.

2. Compounds

Compounds of the invention include crystalline forms I, II, and III of 2-(3-(4-(7H-pyrrolo[2,3-d]pyrimidin-4-yl)-1H-pyrazol-1-yl)-1-(cyclopropylsulfonyl)azetidin yl)acetonitrile. Crystalline forms of 2-(3-(4-(7H-pyrrolo[2,3-d]pyrimidin-4-yl)-1H-pyrazol-1-yl)-1-(cyclopropylsulfonyl)

azetidin-3-yl)acetonitrile are desired to provide for efficiency and reproducibility of production of pharmaceutical formulations and for pharmaceutical compositions with suitable stability.

2-(3-(4-(7H-pyrrolo[2,3-d]pyrimidin-4-yl)-1H-pyrazol-1-yl)-1-(cyclopropylsulfonyl)azetidin-3-yl)acetonitrile is also known by the names 2-[1-cyclopropylsulfonyl-3-[4-(7H-pyrrolo[2,3-d]pyrimidin-4-yl)pyrazol-1-yl]azetidin-3-yl]acetonitrile and 2-(1-cyclopropylsulfonyl-3-pyrazol-1-yl-(4-(7H-pyrrolo[2,3-d]pyrimidin azetidin-3-yl)acetonitrile and for clarity is the compound of the formula (I), below:

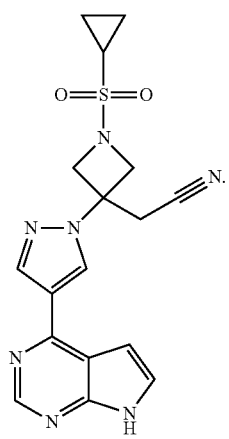

(I)

In a preferred embodiment, a compound of the invention is crystalline form I 2-(3-(4-(7H-pyrrolo[2,3-d]pyrimidin-4-yl)-1H-pyrazol-1-yl)-1-(cyclopropylsulfonyl)azetidin-3-yl)acetonitrile as described herein. Crystalline form I 2-(3-(4-(7H-pyrrolo[2,3-d]pyrimidin-4-yl)-1H-pyrazol-1-yl)-1-(cyclopropylsulfonyl)azetidin-3-yl)acetonitrile is an anhydrate.

In another preferred embodiment, a compound of the invention is crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile as described herein. Crystalline form II 2-(3-(4-(7H-pyrrolo[2,3-d]pyrimidin yl)-1H-pyrazol-1-yl)-1-(cyclopropylsulfonyl)azetidin-3-yl)acetonitrile is also an anhydrate.

In another preferred embodiment, a compound of the invention is crystalline form III 2-(3-(4-(7H-pyrrolo[2,3-d]pyrimidin-4-yl)-1H-pyrazol-1-yl)-1-(cyclopropylsulfonyl)azetidin-3-yl)acetonitrile as described herein. Crystalline form III 2-(3-(4-(7H-pyrrolo[2,3-d]pyrimidin yl)-1H-pyrazol-1-yl)-1-(cyclopropylsulfonyl)azetidin-3-yl)acetonitrile is a hydrated form.

Forms I, II, and III as well as other polymorphic forms of 2-(3-(4-(7H-pyrrolo[2,3-d]pyrimidin-4-yl)-1H-pyrazol-1-yl)-1-(cyclopropylsulfonyl)azetidin-3-yl)acetonitrile can be characterized by X-ray diffraction. The peaks were measured using a powder diffractometer equipped with a copper source, primary beam monochromator, and position sensitive detector. The incident beam was collimated using a 1° divergence slit. The source was operated at 40 kV and 40 mA. X-ray powder diffraction data were collected from 2.5 degrees to 50 degrees using a step width of 0.02 degree and a 37 second step time. Alternately, peaks were measured using a powder diffractometer equipped with a copper source, primary beam monochromator, and position sensitive detector. The incident beam was collimated using a 1° divergence slit. The source was operated at 40 kV and 40 mA. X-ray powder diffraction data were collected from 1.5 degrees to 50 degrees using a step width of 0.02 degree and a 12 second step time.

It is recognized that the relative intensity of X-ray diffraction peaks can be dependent on preferred orientation and other factors such a particle size. Where the effects of preferred orientation and/or particle size are present, peak intensities may be altered, but the characteristic peak positions of the polymorph are unchanged. See, e.g., The United States Pharmacopoeia #24, National Formulary #19, pages 1843-1844, 2000. Therefore, a sample of form I or form II or form III 2-(3-(4-(7H-pyrrolo[2,3-d]pyrimidin-4-yl)-1H-pyrazol-1-yl)-1-(cyclopropylsulfonyl)azetidin-3-yl)acetonitrile may require processing to mitigate such factors, such as grinding the sample in an agate mortar and pestle or other measures. It is understood that differences in relative intensity of the diffraction peaks does not preclude an acquired pattern from being consistent with form I or form II or form III 2-(3-(4-(7H-pyrrolo[2,3-d]pyrimidin yl)-1H-pyrazol-1-yl)-1-(cyclopropylsulfonyl)azetidin-3-yl)acetonitrile.

Furthermore, it is also well known in the crystallography art that, for any given crystal form, the angular peak positions may vary slightly. For example, peak positions can shift due to sample displacement or a variation in the temperature or relative humidity at which a sample is analyzed. In the present case, a peak position variability of ±0.2° in 2θ will take into account these potential variations without hindering the unequivocal identification of the crystalline form of the present disclosure.

Form I, II, or III 2-(3-(4-(7H-pyrrolo[2,3-d]pyrimidin-4-yl)-1H-pyrazol-1-yl)-1-(cyclopropylsulfonyl)azetidin-3-yl)acetonitrile can also be characterized by differential scanning calorimetry. DSC can be carried out in closed (hermetically sealed) gold crucibles or aluminum pans with a pinhole; sample filled under ambient conditions or $N_2$ flow (for 3-10 minutes); heating rate of 10° C./minute from −50° C. to 300° C.

Form I

Crystalline form I 2-(3-(4-(7H-pyrrolo[2,3-d]pyrimidin-4-yl)-1H-pyrazol-1-yl)-1-(cyclopropylsulfonyl)azetidin-3-yl)acetonitrile was found to have the following peaks in degrees 2-theta (° 2θ) having (relative intensity of greater than about 10% of the largest peak, $I_0/I_{100}$%): 12.72° (43.1%), 14.04° (61.3%), 17.56° (20.8%), 20.33° (87.4%), 24.50° (100%), and 25.83° (94.9%) (±0.2° 2θ).

The present disclosure provides a substantially polymorphically pure form I 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising a peak at 12.72°, 14.04°, 17.56°, 20.33°, 24.50°, or 25.83° 2θ (±0.2° 2θ). More particularly, the present disclosure provides substantially polymorphically pure form I 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 12.72° and 24.50° (±0.2° 2θ) or comprising peaks at 20.33° and 24.50° (±0.2° 2θ) or comprising peaks at 12.72° and 20.33° (±0.2° 2θ).

As used herein, the term "form I 2-(3-(4-(7H-pyrrolo[2,3-d]pyrimidin-4-yl)-1H-pyrazol-1-yl)-1-(cyclopropylsulfonyl)azetidin-3-yl)acetonitrile" includes the term "substantially polymorphically pure form I 2-(3-(4-(7H-pyrrolo[2,3-d]pyrimidin-4-yl)-1H-pyrazol-1-yl)-1-(cyclopropylsulfonyl)azetidin-3-yl)acetonitrile."

Form II

Crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile was found to have the following peaks in degrees 2-theta (° 2θ) having (relative intensity of greater than about 10% of the largest peak, $I_0/I_{100}$%): 5.34° (16.2%); 10.68° (26.2%); 14.26° (20.8%); 16.06° (13.5%); 16.39° (17.9%); 16.48° (18.6%); 18.26° (19.5%); 18.65° (43.4%); 19.03° (100.0%); 21.05° (10.2%); 21.15° (9.9%); 21.45° (9.0%); 21.76° (20.5%); 22.45° (9.6%); 22.68° (22.5%); 23.23° (11.1%); 23.72° (12.3%); 24.90° (11.7%); 25.08° (9.2%); 26.75° (30.7%); and 31.18° (10.1%); (±0.2° 2θ).

The present disclosure provides a substantially polymorphically pure form II 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising a peak at 5.34°, 10.68°, 14.26°, 16.06°, 16.39°, 16.48°, 18.26°, 18.65°, 19.03°, 21.05°, 21.76°, 22.68°, or 26.75° (±0.2° 2θ). More particularly, the present disclosure provides substantially polymorphically pure form II 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 18.65° and 10.68° (±0.2° 2θ) or comprising peaks at 18.65° and 21.76° (±0.1° 2θ) or comprising peaks at 18.65° and 22.68° (±0.1° 2θ) or comprising peaks at 26.75° and 21.76° (±0.2° 2θ).

As used herein, the term "form II 2-(3-(4-(7H-pyrrolo[2,3-d]pyrimidin-4-yl)-1H-pyrazol-1-yl)-1-(cyclopropylsulfonyl)azetidin-3-yl)acetonitrile" includes the term "substantially polymorphically pure form II 2-(3-(4-(7H-pyrrolo[2,3-d]pyrimidin-4-yl)-1H-pyrazol-1-yl)-1-(cyclopropylsulfonyl)azetidin-3-yl)acetonitrile."

Form III

Crystalline form III 2-(3-(4-(7H-pyrrolo[2,3-d]pyrimidin-4-yl)-1H-pyrazol-1-yl)-1-(cyclopropylsulfonyl)azetidin-3-yl)acetonitrile was found to have the following peaks in degrees 2-theta (° 2θ) having (relative intensity of greater than about 10% of the largest peak, $I_0/I_{100}$%): 11.08° (62.3%); 12.32° (15.9%); 13.28° (13.7%); 14.06° (15.3%); 14.73° (32.8%); 17.86° (16.9%); 18.06° (46.4%); 18.27° (18.1%); 18.51° (35.2%); 18.91° (10.9%); 20.36° (15.8%); 21.48° (12.7%); 22.24° (26.9%); 22.69° (100%); 23.40° (10.2%); 24.76° (18.8%); 25.48° (55.4%); 25.97° (12.6%); 26.70° (12.5%); and 28.04° (12.8%); (±0.2° 2θ).

The present disclosure provides a substantially polymorphically pure form III 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising a peak at 11.08°, 14.73°, 18.06°, 18.27°, 18.51°, 22.24°, 22.69°, 24.76°, 25.48°, or 28.04° (±0.2° 2θ). More particularly, the present disclosure provides substantially polymorphically pure form III 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 11.08° and 22.69°; (±0.2° 2θ) or comprising peaks at 14.73° and 22.69° (±0.2° 2θ) or comprising peaks at 22.69° and 25.48° (±0.2° 2θ) or comprising peaks at 11.08° and 18.06° (±0.2° 2θ) or comprising peaks at 11.08° and 25.48° (±0.2° 2θ).

As used herein, the term "form III 2-(3-(4-(7H-pyrrolo[2,3-d]pyrimidin-4-yl)-1H-pyrazol-1-yl)-1-(cyclopropylsulfonyl)azetidin-3-yl)acetonitrile" includes the term "substantially polymorphically pure form III 2-(3-(4-(7H-pyrrolo[2,3-d]pyrimidin-4-yl)-1H-pyrazol-1-yl)-1-(cyclopropylsulfonyl)azetidin-3-yl)acetonitrile."

The skilled artisan will appreciate that compounds may exist as tautomers. All tautomeric forms the compounds of the invention are contemplated to be within the scope of the present disclosure.

Compounds of the invention also include all isotopic variations, in which at least one atom of the predominant atom mass is replaced by an atom having the same atomic number, but an atomic mass different from the predominant atomic mass. Use of isotopic variations (e.g., deuterium, $^2H$) may afford greater metabolic stability. Additionally, certain isotopic variations of the compounds of the invention may incorporate a radioactive isotope (e.g., tritium, $^3H$, or $^{14}C$), which may be useful in drug and/or substrate tissue distribution studies. Substitution with positron emitting isotopes, such as $^{11}C$, $^{18}F$, $^{15}O$ and $^{13}N$, may be useful in Positron Emission Topography (PET) studies.

3. PROCESSES TO MAKE CRYSTALLINE FORMS

Form I Processes

Crystalline form I 2-(3-(4-(7H-pyrrolo[2,3-d]pyrimidin-4-yl)-1H-pyrazol-1-yl)-1-(cyclopropylsulfonyl)azetidin-3-yl)acetonitrile may be prepared by crystallization under controlled conditions. The present disclosure also provides a process for making substantially polymorphically pure crystalline form I 2-(3-(4-(7H-pyrrolo[2,3-d]pyrimidin-4-yl)-1H-pyrazol-1-yl)-1-(cyclopropylsulfonyl)azetidin-3-yl)acetonitrile, comprising crystallizing from a mixture of acetone and heptane as an anti-solvent. In a preferred embodiment, form I 2-(3-(4-(7H-pyrrolo[2,3-d]pyrimidin-4-yl)-1H-pyrazol-1-yl)-1-(cyclopropylsulfonyl)azetidin-3-yl) acetonitrile can also be obtained by dehydration of Form III samples, typically be heating at temperatures of from about 40° C. to about 80° C. under vacuum.

Form II Processes

Crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile may be prepared by crystallization under controlled conditions by crystallization from a solvent or a mixture of solvents. The present disclosure also provides a process for making substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile, comprising crystallizing from a solvent or a mixture of solvents further containing water and having a water activity of less than 0.7. In practice suitable solvents are selected from the group consisting of $C_{1-5}$ alcohol, $C_{2-8}$ alkyl ether, $C_{2-8}$ alkyl acetate, $C_{2-5}$ alkyl cyanide, $C_{3-9}$ alkyl ketone, and aromatic solvent; each having a water activity of less than about 0.7.

In a preferred embodiment, the present disclosure also provides a process for making substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile, comprising crystallizing from a solvent or a mixture of solvents further containing water and having a water activity of less than 0.5.

The use of an anti-solvent may be advantageous. As used in this context an "anti-solvent" refers to a solvent in which 2-(3-(4-(7H-pyrrolo[2,3-d]pyrimidin-4-yl)-1H-pyrazol-1-yl)-1-(cyclopropylsulfonyl)azetidin-3-yl)acetonitrile is significantly less soluble relative to the selected solvent(s). Preferably, when an anti-solvent is used it is miscible with the selected solvent. While anti-solvents may be used, care must be taken that the selected anti-solvent(s) does not increase the water activity above the desired level.

It is understood that the water activity that provides substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile is temperature dependent. Higher temperatures of the final state of the crystallization can tolerate higher water activity. Thus, a water activity of about 0.7 is effective at temperatures of the final state of the crystallization of greater than about 40° C.

Because recoveries are higher at lower temperatures, in a preferred embodiment, the present disclosure also provides a process for making substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile, comprising crystallizing from a solvent or a mixture of solvents having a water activity of less than 0.5. Typically, a water activity of about 0.5 is effective at temperatures of the final state of the crystallization of less than about 25° C.

Preferred solvents are selected from the group consisting of $C_{1-5}$ alcohol and $C_{2-5}$ alkyl cyanide; each having a water activity of less than about 0.7. An even more preferred solvent is selected from the group consisting of $C_{1-5}$ alcohol and $C_{2-5}$ alkyl cyanide; each having a water activity of less than about 0.5.

In a particular embodiment, the present disclosure also provides a process of making substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile, comprising crystallizing from acetonitrile further comprising water having a water activity of less than 0.7.

In another particular embodiment, the present disclosure also provides a process of making substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile, comprising crystallizing from acetonitrile further comprising water having a water activity of less than 0.5.

The present disclosure also provides a process of making substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile, comprising crystallizing from acetonitrile further comprising water. Care must be taken to avoid the formation of undesired hydrated crystalline forms. Thus, preferred embodiments for crystallizing from acetonitrile further comprising water utilize a v/v ratio of 92-97 acetonitrile to 8-3 water; more preferred, crystallizing from acetonitrile further comprising water in a v/v ratio of 95-97 acetonitrile to 5-3 water. The use of 96:4 (v/v) acetonitrile/water has been found in practice to have a most favorable volume efficiency at temperatures below about 20° C.

Thus, an even more preferred process for making substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile comprises, crystallizing from acetonitrile further comprising water in a v/v ratio of about 96 acetonitrile to about 4 water.

Optionally, the crystallization may be seeded with form II 2-(3-(4-(7H-pyrrolo[2,3-d]pyrimidin-4-yl)-1H-pyrazol-1-yl)-1-(cyclopropylsulfonyl)azetidin-3-yl)acetonitrile.

Crystallization by precipitation from a solution and slurrying techniques are contemplated to be within the scope of the present process. Where the crystallization involves complete dissolution, slow cooling is preferred at rates of between 0.2° C./minute and 0.02° C./minute. Crystallization to give form II does not require complete dissolution. Slurry processes can be used. A slurry can be formed by processing without complete dissolution or by complete dissolution followed by processing after initial precipitation. In a slurry process the volume should be sufficient to provide free-flowing slurry. The volume of solvent is not critical but should be kept to a minimal amount as a matter of convenience. The water activity of the solvent(s) used must take into account water including water that may be released from a hydrated starting material. Optionally, a slurry crystallization process may be seeded with form II 2-(3-(4-(7H-pyrrolo[2,3-d]pyrimidin-4-yl)-1H-pyrazol-1-yl)-1-(cyclopropylsulfonyl)azetidin-3-yl)acetonitrile.

In one embodiment non-form II containing 2-(3-(4-(7H-pyrrolo[2,3-d]pyrimidin-4-yl)-1H-pyrazol-1-yl)-1-(cyclopropylsulfonyl)azetidin-3-yl)acetonitrile is crystallized by slurry at temperature of about 50° C. or higher and optional cooling to recover the final product. In another embodiment non-form II 2-(3-(4-(7H-pyrrolo[2,3-d]pyrimidin-4-yl)-1H-pyrazol-1-yl)-1-(cyclopropylsulfonyl)azetidin-3-yl)acetonitrile is crystallized by slurry from a solvent at temperature of about room temperature. Optionally, the crystallization may be seeded with form II 2-(3-(4-(7H-pyrrolo[2,3-d]pyrimidin-4-yl)-1H-pyrazol-1-yl)-1-(cyclopropylsulfonyl)azetidin-3-yl)acetonitrile. Such slurry processes generally require 2 to 14 days.

Form III Processes

Crystalline form III 2-(3-(4-(7H-pyrrolo[2,3-d]pyrimidin-4-yl)-1H-pyrazol-1-yl)-1-(cyclopropylsulfonyl)azetidin-3-yl)acetonitrile may be prepared by crystallization under controlled conditions by crystallization from a solvent or a mixture of solvents. The present disclosure also provides a process for making substantially polymorphically pure crystalline form III 2-(3-(4-(7H-pyrrolo[2,3-d]pyrimidin-4-yl)-1H-pyrazol-1-yl)-1-(cyclopropylsulfonyl)azetidin-3-yl)acetonitrile, comprising crystallizing from a solvent or a mixture of solvents further containing water and having a water activity of greater than 0.9. In practice suitable solvents are selected from the group consisting of water, $C_{1-5}$ alcohol, $C_{2-8}$ alkyl acetate, $C_{2-5}$ alkyl cyanide, and $C_{3-9}$ alkyl ketone; each having a water activity of greater than about 0.9.

The use of an anti-solvent may be advantageous. As used in this context an "anti-solvent" refers to a solvent in which 2-(3-(4-(7H-pyrrolo[2,3-d]pyrimidin-4-yl)-1H-pyrazol-1-yl)-1-(cyclopropylsulfonyl)azetidin-3-yl)acetonitrile is significantly less soluble relative to the selected solvent(s). Preferably, when an anti-solvent is used it is miscible with the selected solvent.

While anti-solvents may be used, care must be taken that the selected anti-solvent(s) does not decrease the water activity below the desired level.

A preferred solvent is selected from the group consisting of $C_{1-5}$ alcohol having a water activity of greater than about 0.9.

Crystallization from a solution and slurrying techniques are contemplated to be within the scope of the present process. Where the crystallization involves complete dissolution, slow cooling is preferred at rates of between 0.2° C./minute and 0.02° C./minute. Crystallization to give form III does not require complete dissolution. Slurry processes can be used. A slurry can be formed by processing without complete dissolution or by complete dissolution followed by processing after initial precipitation. In a slurry process the volume should be sufficient to provide free-flowing slurry. The volume of solvent is not critical but should be kept to a minimal amount as a matter of convenience. Optionally, a slurry crystallization process may be seeded with form III 2-(3-(4-(7H-pyrrolo[2,3-d]pyrimidin-4-yl)-1H-pyrazol-1-yl)-1-(cyclopropylsulfonyl)azetidin-3-yl)acetonitrile.

In one embodiment non-form III containing 2-(3-(4-(7H-pyrrolo[2,3-d]pyrimidin-4-yl)-1H-pyrazol-1-yl)-1-(cyclopropylsulfonyl)azetidin-3-yl)acetonitrile is crystallized by slurry from a solvent having a water activity greater than 0.9 at temperature of about room temperature. Optionally, the crystallization may be seeded with form III 2-(3-(4-(7H-pyrrolo[2,3-d]pyrimidin-4-yl)-1H-pyrazol-1-yl)-1-(cyclopropylsulfonyl)azetidin-3-yl)acetonitrile. Such slurry processes generally require 2 to 10 days.

Care must be taken when drying form III 2-(3-(4-(7H-pyrrolo[2,3-d]pyrimidin-4-yl)-1H-pyrazol-1-yl)-1-(cyclopropylsulfonyl)azetidin-3-yl)acetonitrile to avoid conversion to form I, preferably under vacuum at temperatures below 20° C.

4. SYNTHETIC METHODS

The present disclosure provides a process for making 2-(3-(4-(7H-pyrrolo[2,3-d]pyrimidin-4-yl)-1H-pyrazol-1-yl)-1-(cyclopropylsulfonyl)azetidin-3-yl)acetonitrile as depicted in Scheme A.

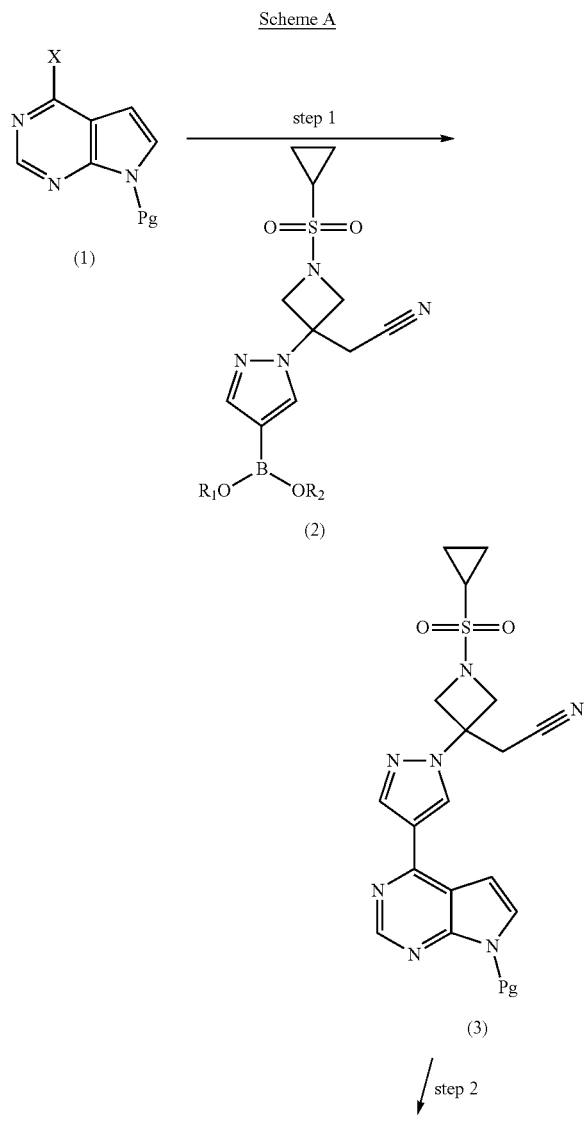

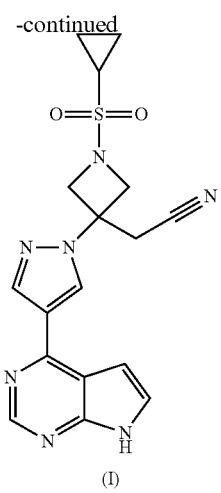

In Scheme A, step 1, a compound of formula (1) is reacted with a compound of formula (2) in the presence of a suitable catalyst to give a compound of formula (3). A compound of formula (1) is one wherein X is selected from the group consisting of tosylate, triflate, chloro, bromo, and iodo and Pg is a protecting group. In practice a compound of formula (1) wherein X is bromo or chloro are preferred and chloro is even more preferred. A variety of protecting groups are suitable. The selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999). For example, t-BOC, 2-(trimethylsilyl)ethoxymethyl, and N-pivaloyloxymethyl are useful, to mention only a few. In practice, a t-BOC group is preferred. A compound of formula (2) is one wherein $R_1$ and $R_2$ are independently selected from the group consisting of hydrogen and $C_{1-6}$ alkyl; or $R_1$ and $R_2$, together with the oxygen atoms to which they are attached and the boron atom, form a 5- to 6-membered heterocyclic ring, which is optionally substituted with 1, 2, 3, or 4 $C_{1-4}$ alkyl groups. As will be appreciated by the skilled person the depicted reaction in step 1 is the well-known Suzuki reaction. A variety of suitable catalysts are available. Both nickel and palladium catalysts are useful, however, palladium catalysts are preferred. A number of suitable palladium(0) and palladium(II) catalysts are known in the art. For example, tetrakis(triphenylphosphine)palladium(0), tetrakis(triphenylphosphine)palladium(II)chloride, 4,5-bis(diphenylphosphino)-9,9-dimethylxanthene, and dichloromethane [1,1'-bis(diphenylphosphino)ferrocene]dichloropalladium(II) (1:1).

The reaction is typically carried out in a solvent, including a large variety of organic solvents. The solvent may contain water. For example, suitable solvents include 1,4-dioxane, THF, 1-butanol, 1,2-dimethoxyethane (DME), 2-propanol, toluene, or ethanol, or a combinations thereof. Typical palladium catalyst is used in amounts from about 0.01 to about 0.1 equivalents.

The reaction is carried out in the presence of base. Both organic and inorganic bases can be used, for example, alkali metal carbonates and alkali metal bicarbonates as well as bases such as cesium carbonate are used. The reaction is typically conducted at a temperature of about 40° C. to about 100° C. and generally requires 1 to 18 hours.

5. PHARMACEUTICAL COMPOSITIONS

The present disclosure provides a pharmaceutical composition comprising 2-(3-(4-(7H-pyrrolo[2,3-d]pyrimidin-4-yl)-1H-pyrazol-1-yl)-1-(cyclopropylsulfonyl)azetidin-3-yl) acetonitrile or a salt thereof, and an acceptable excipient. In a preferred embodiment, the present disclosure provides a pharmaceutical composition comprising crystalline form I or form II or form III 2-(3-(4-(7H-pyrrolo[2,3-d]pyrimidin-4-yl)-1H-pyrazol-1-yl)-1-(cyclopropylsulfonyl)azetidin-3-yl)acetonitrile and an acceptable excipient. In another preferred embodiment, the present disclosure provides a pharmaceutical composition comprising crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile, and at least one acceptable excipient. In another preferred embodiment, the present disclosure provides a pharmaceutical composition comprising substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl) acetonitrile, and at least one acceptable excipient.

The compounds of the invention can be administered alone or in the form of a composition. In practice, the compounds of the invention are usually administered in the form of compositions, that is, in admixture with at least one acceptable excipient. The proportion and nature of any acceptable excipient(s) are determined by the properties of the selected compound of the invention, the chosen route of administration, and standard practice as in the veterinary and pharmaceutical fields.

In effecting treatment of a subject in need of such treatment, a compound of the invention can be administered in any form and route which makes the compound bioavailable.

The compounds of the invention can be administered by a variety of routes, including orally, in particularly by tablets and capsules. The compounds of the invention can be administered parenteral routes, more particularly by inhalation, subcutaneously, intramuscularly, intravenously, intraarterially, transdermally, intranasally, rectally, vaginally, occularly, topically, sublingually, and buccally, intraperitoneally, intraadiposally, intrathecally and via local delivery for example by catheter or stent.

One skilled in the art can readily select the proper form and route of administration depending upon the particular characteristics of the compound selected, the disorder or condition to be treated, the stage of the disorder or condition, and other relevant circumstances. The pharmaceutical compositions of the invention may be administered to the patient, for example, in the form of tablets, capsules, cachets, papers, lozenges, wafers, elixirs, ointments, transdermal patches, aerosols, inhalants, suppositories, drenches, solutions, and suspensions.

In one embodiment, the composition is adapted for oral administration, such as a tablet or a capsule or a liquid formulation, for example, a solution or suspension, adapted for oral administration. In one embodiment, the composition is adapted for oral administration, such as chewable formulation, adapted for oral administration. In still another embodiment, the composition is a liquid or semi-solid formulation, for example, a solution or suspension or a paste, adapted for parenteral administration.

The compositions of the present disclosure are prepared in a manner well known in the veterinary and pharmaceutical art and include at least one of the compounds of the invention as the active ingredient. The amount of a compound of the present disclosure may be varied depending upon its particular form and may conveniently be between 1% to about 50% of the weight of the unit dose form. The present pharmaceutical compositions are preferably formulated in a unit dose form, each dose typically containing from about 0.25 mg to about 10 mg of a compounds of the invention. One or more unit dose form(s) may be taken to affect the treatment dosage.

6. METHODS OF USE

The present disclosure provides a method of treating dermatological conditions, comprising administering to a non-human mammal in need thereof an effective amount of a compound of the invention.

In certain embodiments, the present disclosure provides a method of treating dermatological conditions [e.g., skin disorders such as psoriasis (for example, psoriasis vulgaris), atopic dermatitis, skin rash, skin irritation, skin sensitization (e.g., contact dermatitis or allergic contact dermatitis), pruritus, including pruritus associated with allergic dermatitis, and allergic reactions], comprising administering to a non-human mammal in need thereof an effective amount of 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof. A preferred non-human mammal is a dog. In certain embodiments, the dog is at least 9 months of age, or at least 12 months of age.

In a preferred embodiment, the present disclosure provides a method of treating dermatological conditions [e.g., skin disorders such as psoriasis (for example, psoriasis vulgaris), atopic dermatitis, skin rash, skin irritation, skin sensitization (e.g., contact dermatitis or allergic contact dermatitis), pruritus, including pruritus associated with allergic dermatitis, and allergic reactions], comprising administering to a non-human mammal in need thereof an effective amount of crystalline form I or form II or form III 2-(3-(4-(7H-pyrrolo[2,3-d]pyrimidin-4-yl)-1H-pyrazol-1-yl)-1-(cyclopropylsulfonyl)azetidin-3-yl)acetonitrile. A preferred non-human mammal is a dog. In certain embodiments, the dog is at least 9 months of age, or at least 12 months of age.

In a particularly preferred embodiment, the present disclosure provides a method of treating dermatological conditions [e.g., skin disorders such as psoriasis (for example, psoriasis vulgaris), atopic dermatitis, skin rash, skin irritation, skin sensitization (e.g., contact dermatitis or allergic contact dermatitis), pruritus, including pruritus associated with allergic dermatitis, and allergic reactions], comprising administering to a non-human mammal in need thereof an effective amount of crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile. A preferred non-human mammal is a dog. In certain embodiments, the dog is at least 9 months of age, or at least 12 months of age.

In a further particularly preferred embodiment, the present disclosure provides a method of treating dermatological conditions [e.g., skin disorders such as psoriasis (for example, psoriasis vulgaris), atopic dermatitis, skin rash, skin irritation, skin sensitization (e.g., contact dermatitis or allergic contact dermatitis), pruritus, including pruritus associated with allergic dermatitis, and allergic reactions], comprising administering to a non-human mammal in need thereof an effective amount of substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile. A preferred non-human mammal is a dog. In certain embodiments, the dog is at least 9 months of age, or at least 12 months of age.

In certain embodiments, the present disclosure provides a method of treating atopic dermatitis comprising administering to a non-human mammal in need thereof an effective amount of 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof. In a preferred embodiment, the present disclosure provides a method of treating atopic dermatitis comprising administering to a non-human mammal in need thereof an effective amount of crystalline form I or form II or form III 2-(3-(4-(7H-pyrrolo[2,3-d]pyrimidin-4-yl)-1H-pyrazol-1-yl)-1-(cyclopropylsulfonyl)azetidin-3-yl)acetonitrile. In a particularly preferred embodiment, the present disclosure provides a method of treating atopic dermatitis, comprising administering to a non-human mammal in need thereof an effective amount of crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile. In a further particularly preferred embodiment, the present disclosure provides a method of treating atopic dermatitis, comprising administering to a non-human mammal in need thereof an effective amount of substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile. A preferred non-human mammal is a dog. In certain embodiments, the dog is at least 9 months of age, or at least 12 months of age.

In certain embodiments, the present disclosure provides a method of treating pruritus associated with allergic dermatitis comprising administering to a non-human mammal in need thereof an effective amount of 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof. In a preferred embodiment, the present disclosure provides a method of treating pruritus associated with allergic dermatitis comprising administering to a non-human mammal in need thereof an effective amount of crystalline form I or form II or form III 2-(3-(4-(7H-pyrrolo[2,3-d]pyrimidin-4-yl)-1H-pyrazol-1-yl)-1-(cyclopropylsulfonyl)azetidin-3-yl)acetonitrile. In a particularly preferred embodiment, the present disclosure provides a method of treating pruritus associated with allergic dermatitis, comprising administering to a non-human mammal in need thereof an effective amount of crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile. In a further particularly preferred embodiment, the present disclosure provides a method of treating pruritus associated with allergic dermatitis, comprising administering to a non-human mammal in need thereof an effective amount of substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile. A preferred non-human mammal is a dog. In certain embodiments, the dog is at least 9 months of age, or at least 12 months of age.

An effective amount can range from, for example, 0.5 mg to 100 mg. Specific amounts can be determined by the skilled person. Although these dosages are based on a patient having a mass of about 0.5 kg to about 80 kg, the diagnostician will be able to determine the appropriate dose for a subject whose mass falls outside of this weight range. An effective amount can range from, for example, 0.1 mg to 1.2 mg/kg of the patient, 0.3 mg to 1.0 mg/kg of the patient, or 0.4 mg to 0.6 mg/kg of the patient. The dosing regimen can be, for example, daily, twice daily, weekly, or monthly administration.

In certain embodiments, the present disclosure provides 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof for use in treating dermatological conditions [e.g., skin disorders such as psoriasis (for example, psoriasis vulgaris), atopic dermatitis, skin rash, skin irritation, skin sensitization (e.g., contact dermatitis or allergic contact dermatitis), pruritus, including pruritus associated with allergic dermatitis, and allergic reactions] in a non-human mammal. A preferred non-human mammal is a dog. In certain embodiments, the dog is at least 9 months of age, or at least 12 months of age.

In a preferred embodiment, the present disclosure provides crystalline form I or form II or form III 2-(3-(4-(7H-pyrrolo[2,3-d]pyrimidin-4-yl)-1H-pyrazol-1-yl)-1-(cyclopropylsulfonyl)azetidin-3-yl)acetonitrile for use in treating dermatological conditions [e.g., skin disorders such as psoriasis (for example, psoriasis vulgaris), atopic dermatitis, skin rash, skin irritation, skin sensitization (e.g., contact dermatitis or allergic contact dermatitis), pruritus, including pruritus associated with allergic dermatitis, and allergic reactions] in a non-human mammal. A preferred non-human mammal is a dog. In certain embodiments, the dog is at least 9 months of age, or at least 12 months of age.

In a particularly preferred embodiment, the present disclosure provides crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile for use in treating dermatological conditions [e.g., skin disorders such as psoriasis (for example, psoriasis vulgaris), atopic dermatitis, skin rash, skin irritation, skin sensitization (e.g., contact dermatitis or allergic contact dermatitis), pruritus, including pruritus associated with allergic dermatitis, and allergic reactions] in a non-human mammal. A preferred non-human mammal is a dog. In certain embodiments, the dog is at least 9 months of age, or at least 12 months of age.

In a further particularly preferred embodiment, the present disclosure provides substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile for use in treating dermatological conditions [e.g., skin disorders such as psoriasis (for example, psoriasis vulgaris), atopic dermatitis, skin rash, skin irritation, skin sensitization (e.g., contact dermatitis or allergic contact dermatitis), pruritus, including pruritus associated with allergic dermatitis, and allergic reactions] in a non-human mammal. A preferred non-human mammal is a dog. In certain embodiments, the dog is at least 9 months of age, or at least 12 months of age.

In certain embodiments, the present disclosure provides 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof for use in the treatment of atopic dermatitis in a non-human mammal. In a preferred embodiment, the present disclosure provides crystalline form I or form II or form III 2-(3-(4-(7H-pyrrolo[2,3-d]pyrimidin-4-yl)-1H-pyrazol-1-yl)-1-(cyclopropylsulfonyl)azetidin-3-yl)acetonitrile for use in the treatment of atopic dermatitis in a non-human mammal. In a particularly preferred embodiment, the present disclosure provides crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile for use in the treatment of atopic dermatitis in a non-human mammal. In a further particularly preferred embodiment, the present disclosure provides substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile for use in the treatment of atopic dermatitis in a non-human mammal. A preferred non-human mammal is a dog. In certain embodiments, the dog is at least 9 months of age, or at least 12 months of age.

In certain embodiments, the present disclosure provides 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof for use in the treatment of pruritus associated with allergic dermatitis in a non-human mammal. In a preferred embodiment, the present disclosure provides crystalline form I or form II or form III 2-(3-(4-(7H-pyrrolo[2,3-d]pyrimidin-4-yl)-1H-pyrazol-1-yl)-1-(cyclopropylsulfonyl)azetidin-3-yl)acetonitrile for use in the treatment of pruritus associated with allergic dermatitis in a non-human mammal. In a particularly preferred embodiment, the present disclosure provides crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile for use in the treatment of pruritus associated with allergic dermatitis in a non-human mammal. In a further particularly preferred embodiment, the present disclosure provides substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile for use in the treatment of pruritus associated with allergic dermatitis in a non-human mammal. A preferred non-human mammal is a dog. In certain embodiments, the dog is at least 9 months of age, or at least 12 months of age.

In certain embodiments, the present disclosure provides use of 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof for the manufacture of a medicament for the treatment of dermatological conditions [e.g., skin disorders such as psoriasis (for example, psoriasis vulgaris), atopic dermatitis, skin rash, skin irritation, skin sensitization (e.g., contact dermatitis or allergic contact dermatitis), pruritus, including pruritus associated with allergic dermatitis, and allergic reactions] in a non-human mammal. A preferred non-human mammal is a dog. In certain embodiments, the dog is at least 9 months of age, or at least 12 months of age.

In a preferred embodiment, the present disclosure provides use of crystalline form I or form II or form III 2-(3-(4-(7H-pyrrolo[2,3-d]pyrimidin-4-yl)-1H-pyrazol-1-yl)-1-(cyclopropylsulfonyl)azetidin-3-yl)acetonitrile for the manufacture of a medicament for the treatment of dermatological conditions [e.g., skin disorders such as psoriasis (for example, psoriasis vulgaris), atopic dermatitis, skin rash, skin irritation, skin sensitization (e.g., contact dermatitis or allergic contact dermatitis), pruritus, including pruritus associated with allergic dermatitis, and allergic reactions] in a non-human mammal. A preferred non-human mammal is a dog. In certain embodiments, the dog is at least 9 months of age, or at least 12 months of age.

In a particularly preferred embodiment, the present disclosure provides use of crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile for the manufacture of a medicament for the treatment of dermatological conditions [e.g., skin disorders such as psoriasis (for example, psoriasis vulgaris), atopic dermatitis, skin rash, skin irritation, skin sensitization (e.g., contact dermatitis or allergic contact dermatitis), pruritus, including pruritus associated with allergic dermatitis, and allergic reactions] in a non-human mammal. A preferred non-human mammal is a dog. In certain embodiments, the dog is at least 9 months of age, or at least 12 months of age.

In a further particularly preferred embodiment, the present disclosure provides use of substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile for the manufacture of a medicament for the treatment of dermatological conditions [e.g., skin disorders such as psoriasis (for example, psoriasis vulgaris), atopic dermatitis, skin rash, skin irritation, skin sensitization (e.g., contact dermatitis or allergic contact dermatitis), pruritus, including pruritus associated with allergic dermatitis, and allergic reactions] in a non-human mammal. A preferred non-human mammal is a dog. In certain embodiments, the dog is at least 9 months of age, or at least 12 months of age.

In certain embodiments, the present disclosure provides use of 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof for the manufacture of a medicament for the treatment of atopic dermatitis in a non-human mammal. In a preferred embodiment, the present disclosure provides use of crystalline form I or form II or form III 2-(3-(4-(7H-pyrrolo[2,3-d]pyrimidin-4-yl)-1H-pyrazol-1-yl)-1-(cyclopropylsulfonyl)azetidin-3-yl)acetonitrile for the manufacture of a medicament for the treatment of atopic dermatitis in a non-human mammal. In a particularly preferred embodiment, the present disclosure provides use of crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile for the manufacture of a medicament for the treatment of atopic dermatitis in a non-human mammal. In a further particularly preferred embodiment, the present disclosure provides use of substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile for the manufacture of a medicament for the treatment of atopic dermatitis in a non-human mammal. A preferred non-human mammal is a dog. In certain embodiments, the dog is at least 9 months of age, or at least 12 months of age.

In certain embodiments, the present disclosure provides use of 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof for the manufacture of a medicament for the treatment of pruritus associated with allergic dermatitis in a non-human mammal. In a preferred embodiment, the present disclosure provides use of crystalline form I or form II or form III 2-(3-(4-(7H-pyrrolo[2,3-d]pyrimidin-4-yl)-1H-pyrazol-1-yl)-1-(cyclopropylsulfonyl)azetidin-3-yl)acetonitrile for the manufacture of a medicament for the treatment of pruritus associated with allergic dermatitis in a non-human mammal. In a particularly preferred embodiment, the present disclosure provides use of crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile for the manufacture of a medicament for the treatment of pruritus associated with allergic dermatitis in a non-human mammal. In a further particularly preferred embodiment, the present disclosure provides use of substantially polymorphically pure crystalline form II 2-(3-(4-(7H-pyrrolo[2,3-d]pyrimidin-4-yl)-1H-pyrazol-1-yl)-1-(cyclopropylsulfonyl)azetidin-3-yl)acetonitrile for the manufacture of a medicament for the treatment of pruritus associated with allergic dermatitis in a non-human mammal. A preferred non-human mammal is a dog. In certain embodiments, the dog is at least 9 months of age, or at least 12 months of age.

7. EXAMPLES

The following examples are provided to illustrate the invention and are not intended to be limiting in any way.

Example 1

2-[1-Cyclopropylsulfonyl-3-[4-(4,4,5,5-tetramethyl-1,3,2-dioxaborolan-2-yl)pyrazol-1-yl]azetidin-3-yl]acetonitrile 2-(1-Cyclopropylsulfonylazetidin-3-ylidene)acetonitrile (850 g) and 4-(4,4,5,5-tetramethyl-1,3,2-dioxaborolan-2-yl)-1H-pyrazole (874 g) were combined in acetonitrile (2.6 L). 1,8-Diazabicyclo[5.4.0]undec-7-ene (65 g) was added and the mixture was heated to 70° C. After 2.5 hours, the reaction mixture was cooled to ambient temperature over about 2 hours. Water (5.2 L) was added slowly to the mixture over about an hour and the mixture was stirred over about 3 hours. The solid that formed was collected by filtration and dried in vacuum at 45° C. for about 24 hours to give 2-[1-cyclopropylsulfonyl-3-[4-(4,4,5,5-tetramethyl-1,3,2-dioxaborolan-2-yl)pyrazol-1-yl]azetidin-3-yl]acetonitrile.

Example 2

2-(3-(4-(7H-pyrrolo[2,3-d]pyrimidin-4-yl)-1H-pyrazol-1-yl)-1-(cyclopropylsulfonyl)azetidin-3-yl)acetonitrile Potassium phosphate (829 g) was combined with water (1 L) and cooled to ambient temperature. THF (2 L) was added. 4-Chloropyrrolo[2,3-d]pyrimidine (200 g) was added followed by addition of di-tert-butyl dicarbonate (344 g). The reaction mixture was stirred at ambient temperature for 24 hours. The reaction mixture was sparged with nitrogen gas for 60 minutes. 2-[1-Cyclopropylsulfonyl-3-[4-(4,4,5,5-tetramethyl-1,3,2-dioxaborolan-2-yl)pyrazol yl]azetidin-3-yl]acetonitrile (562 g) and Pd-134 (6.6 g) were added and the reaction temperature was raised to 60° C. After about 2 hours the aqueous layer was separated and silica thiol (40 g) was added and the reaction was stirred at 60° C. for 18 hours. The reaction mixture was filtered at 60° C. and then the filtrate cooled to 10-20° C. with stirring to give a solid which was collected by filtration and rinsed with cold THF before drying at 40-50° C. under vacuum for 2 hours to give tert-butyl 4-[1-[3-(cyanomethyl)-1-cyclopropylsulfonyl-azetidin-3-yl]pyrazol-4-yl]pyrrolo[2,3-d]pyrimidine-7-carboxylate (540 g).

tert-Butyl 4-[1-[3-(cyanomethyl)-1-cyclopropylsulfonyl-azetidin-3-yl]pyrazol-4-yl]pyrrolo[2,3-d]pyrimidine-7-carboxylate obtained above (540 g) was combined with n-butanol (3 L) and water (770 mL) and heated to 90° C. After 6 hours the reaction was cooled to 80° C. within 30 minutes and then stirred at 80° C. for 30 minute before being cooled to 20° C. over 6 hours and stirred at 10-20° C. for 16 hours to give a solid which was filtered to give the title compound (as a wet cake) 460 g.

Example 3

2-(3-(4-(7H-pyrrolo[2,3-d]pyrimidin-4-yl)-1H-pyrazol-1-yl)-1-(cyclopropylsulfonyl)azetidin-3-yl)acetonitrile Potassium phosphate (829 g) was combined with water (1 L) and cooled to ambient temperature. THF (2 L) was added. 4-Chloropyrrolo[2,3-d]pyrimidine (200 g) was added followed by addition of di-tert-butyl dicarbonate (344 g). The reaction mixture was stirred at ambient temperature for 24 hours. The reaction mixture was sparged with nitrogen gas for 60 minutes. 2-[1-Cyclopropylsulfonyl-3-[4-(4,4,5,5-tetramethyl-1,3,2-dioxaborolan-2-yl)pyrazol-1-yl]azetidin-3-yl]acetonitrile (562 g) and Pd-134 (6.6 g) were added and the reaction temperature was raised to 60° C. After about 2 hours the aqueous layer was separated and silica thiol (40 g) was added and the reaction was stirred at 60° C. for 18 hours. The reaction mixture was filtered at 60° C. and then the filtrate cooled to 10-20° C. with stirring to give a solid which was collected by filtration and rinsed with cold THF before drying at 40-50° C. under vacuum for 2 hours to give tert-butyl 4-[1-[3-(cyanomethyl)-1-cyclopropylsulfonyl-azetidin-3-yl]pyrazol-4-yl]pyrrolo[2,3-d]pyrimidine-7-carboxylate (525 g).

tert-Butyl 4-[1-[3-(cyanomethyl)-1-cyclopropylsulfonyl-azetidin yl]pyrazol-4-yl]pyrrolo[2,3-d]pyrimidine-7-carboxylate obtained above (540 g) was combined with n-butanol (3 L) and water (770 mL) and heated to 90° C. After 6 hours the reaction was cooled to 80° C. within 30 minutes and then stirred at 80° C. for 30 minute before being cooled to 20° C. over 6 hours and stirred at 10-20° C. for 16 hours to give a solid which was filtered to give the title compound (as a wet cake) 454 g.

Example 4

2-(3-(4-(7H-pyrrolo[2,3-d]pyrimidin-4-yl)-1H-pyrazol-1-yl)-1-(cyclopropylsulfonyl)azetidin-3-yl)acetonitrile Form II The wet cakes from Examples 2 and 3 (about 907 g) were combined in acetonitrile (4 L) and stirred at 60° C. for 2 hours. The reaction mixture was cooled to 20° C. over 6 hours and then stirred at 20° C. for 12 hours. The solid was collected by filtration, rinsed with acetonitrile, and dried under vacuum at 50-60° C. for 24 hours to give the title compound (695 g).

Example 5

2-(3-(4-(7H-pyrrolo[2,3-d]pyrimidin-4-yl)-1H-pyrazol-1-yl)-1-(cyclopropylsulfonyl)azetidin-3-yl)acetonitrile Form I 2-(3-(4-(7H-pyrrolo[2,3-d]pyrimidin-4-yl)-1H-pyrazol-1-yl)-1-(cyclopropylsulfonyl)azetidin-3-yl)acetonitrile (104.1 mg) was combined with acetone (8 mL) and heated to 55° C. After 30 minutes, the reaction mixture was cooled at a rate of 0.02° C./minute to a temperature of 30° C. and then at a rate of 0.1° C./minute to a temperature of 5° C. while simultaneously adding heptane (12 mL) at a rate of 2.94 mL/hour to give a solid which was collected by filtration and dried to give the title compound (79.5 mg).

Example 6

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (152.4 mg) was combined with acetonitrile (8.1 mL) and heated to 80° C. After 30 minutes, the reaction mixture was cooled at a rate of 0.05° C./minute to a temperature of 5° C. to give a solid which was collected by filtration and dried to give the title compound (93.4 mg).

Example 7

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (157.8 mg) was combined with acetonitrile/water 96:4 (v/v) (4.2 mL) and heated to 80° C. After 30 minutes, the reaction mixture was cooled at a rate of 0.05° C./minute to a temperature of 5° C. to give a solid which was collected by filtration and dried to give the title compound (89.4 mg).

Example 8

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (5 g) was combined with acetonitrile/water 96:4 (v/v) (100 mL) and heated to 80° C. After about 75 minutes, the reaction mixture was cooled at a rate of 0.20° C./minute to a temperature of 70° C. and then seeds (2 portions of 0.25 g) were added and the cooling was continued at a rate of 0.05° C./minute to a temperature of 8° C. to give a solid. After about 6 hours the solid was collected by filtration and dried to give the title compound (4.88 g).

Example 9

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (20.6 mg) is combined with 4:1 (v/v) methanol/water (0.3 mL) having a water activity of about 0.5 and stir at 25° C. for 4 days, add additional with 4:1 (v/v) methanol/water (0.5 mL) and continue stirring at 25° C. for 6 days and then collect the solid by filter centrifugation (3 minutes, 5000 rpm, 0.2 μm PVDF membrane) to give the title compound.

Example 10

2-(3-(4-(7H-pyrrolo[2,3-d]pyrimidin-4-yl)-1H-pyrazol-1-yl)-1-(cyclopropylsulfonyl)azetidin yl)acetonitrile Form II 2-(3-(4-(7H-pyrrolo[2,3-d]pyrimidin-4-yl)-1H-pyrazol-1-yl) (cyclopropylsulfonyl)azetidin-3-yl)acetonitrile (10 g) was combined with acetonitrile/water 96:4 (v/v) (250 mL) and heated to 72° C. After about 60 minutes, the reaction mixture was cooled at a rate of 0.20° C./minute to a temperature of 65° C. and then seeds (0.10 g) were added and the cooling was continued at a rate of 0.035° C./minute to a temperature of 35° C. to give a solid and then at a rate of 0.125° C./minute to a temperature of 5° C. to give a solid. After about 3 hours the solid was collected by filtration and dried to give the title compound (8.51 g).

Example 11

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (70.3 mg) was combined with 0.2 mL of 9:1 (v/v) acetone/water and heated to 60° C. while stirring. Additional 9:1 (v/v) acetone/water was slowly added a total of about 1.6 mL. The temperature was held at 60° C. for 1.5 hours and then the mixture was cooled at a rate of 0.05° C./minute to 10° C. and held at 10° C. for 2 hours and 45 minutes to give a solid. The solid was collected by filter centrifugation (2 minutes, 5000 rpm) to give the title compound.

Example 12

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (149.8 mg) was combined with acetonitrile (8.0 mL) and heated to 80° C. After 30 minutes, the reaction mixture was cooled at a rate of 0.02° C./minute to a temperature of 55° C. The reaction mixture was then cooled at a rate of 0.1° C./minute over the range 55° C. to 5° C. while simultaneously adding a total of 12 mL of isopropyl acetate at a rate of 1.44 mL/hour over the same duration as the cooling ramp from 55° C. to 5° C. to give a solid which was collected by filtration and dried to give the title compound (94.2 mg).

Example 13

2-(3-(4-(7H-pyrrolo[2,3-d]pyrimidin-4-yl)-1H-pyrazol-1-yl)-1-(cyclopropylsulfonyl)azetidin yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (208.5 mg) was combined with 0.2 mL of 3:1 (v/v) methanol/water and heated to 60° C. while stirring. Additional 3:1 (v/v) methanol/water was slowly added a total of about 23.2 mL. The temperature was held at 60° C. for 30 minutes and then the mixture was cooled at a rate of 0.05° C./minute to 10° C. and held at 10° C. for 20 minutes to give a solid. The solid was collected by filtration to give the title compound.

Example 14

2-(3-(4-(7H-pyrrolo[2,3-d]pyrimidin-4-yl)-1H-pyrazol-1-yl)-1-(cyclopropylsulfonyl)azetidin-3-yl)acetonitrile Form III 2-(3-(4-(7H-pyrrolo[2,3-d]pyrimidin-4-yl)-1H-pyrazol-1-yl)-1-(cyclopropylsulfonyl)azetidin-3-yl)acetonitrile (60 mg) is combined with 2 mL of 5:1 (v/v) 1-butanol/water having a water activity of about 0.9 and stir at room temperature for 10 days and then collect the solid by filter

Example 15

2-(3-(4-(7H-pyrrolo[2,3-d]pyrimidin-4-yl)-1H-pyrazol-1-yl)-1-(cyclopropylsulfonyl)azetidin-3-yl)acetonitrile Form III 2-(3-(4-(7H-pyrrolo[2,3-d]pyrimidin-4-yl)-1H-pyrazol-1-yl)-1-(cyclopropylsulfonyl)azetidin-3-yl)acetonitrile (33 mg) is combined with 0.4 mL of 3:2 (v/v) methanol/water having a water activity of about 0.7 and stir at about 20° C. for 14 days and then collect the solid by filter centrifugation (2 minutes, 4400 rpm, 0.2 μm PTFE membrane) to give the title compound.

Example 16

2-(3-(4-7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.4 mg) is combined with acteophenone (1 mL) and stir at room temperature for 10 days and then collect the solid by filter centrifugation (2 minutes, 5000 rpm, 0.2 μm PTFE membrane) to give the title compound.

Example 17

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (59.9 mg) is combined with butyronitrile (2 mL) and stir at room temperature for 10 days and then collect the solid by filter centrifugation (2 minutes, 5000 rpm, 0.2 μm PTFE membrane) to give the title compound.

Example 18

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.3 mg) is combined with cyclohexanone (1.5 mL) and stir at room temperature for 10 days and then collect the solid by filter centrifugation (2 minutes, 5000 rpm, 0.2 μm PTFE membrane) to give the title compound.

Example 19

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.9 mg) is combined with dioxane (2 mL) and stir at room temperature for 10 days and then collect the solid by filter centrifugation (2 minutes, 5000 rpm, 0.2 μm PTFE membrane) to give the title compound.

Example 20

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.0 mg) is combined with ethyl formate (1.5 mL) and stir at room temperature for 10 days and then collect the solid by filter centrifugation (2 minutes, 5000 rpm, 0.2 μm PTFE membrane) to give the title compound.

Example 21

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (59.4 mg) is combined with methyl acetate (1.5 mL) and stir at room temperature for 10 days and then collect the solid by filter centrifugation (2 minutes, 5000 rpm, 0.2 μm PTFE membrane) to give the title compound.

Example 22

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.5 mg) is combined with nitrobenzene (2 mL) and stir at room temperature for 10 days and then collect the solid by filter centrifugation (2 minutes, 5000 rpm, 0.2 μm PTFE membrane) to give the title compound.

Example 23

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.5 mg) is combined with anisole (0.6 mL) and stir at 40° C. for 6 days and then collect the solid by filter centrifugation (2 minutes, 5000 rpm, 0.2 PTFE membrane) to give the title compound.

Example 24

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl) (cyclopropylsulfonyl)azetidin-3-yl)acetonitrile (59.8 mg) is combined with ethyl formate (0.6 mL) and stir at 40° C. for 6 days and then collect the solid by filter centrifugation (2 minutes, 5000 rpm, 0.22 μm PVDF membrane) to give the title compound.

Example 25

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.5 mg) is combined with isopropyl acetate (0.6 mL) and stir at 40° C. for 6 days and then collect the solid by filter centrifugation (2 minutes, 5000 rpm, 0.22 μm PVDF membrane) to give the title compound.

Example 26

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.4 mg) is combined with isopentanol (1 mL) and stir at 40° C. for 6 days and then collect the solid by filter centrifugation (2 minutes, 5000 rpm, 0.2 μm PTFE membrane) to give the title compound.

Example 27

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.4 mg) is combined with methyl isobutyl ketone (1 mL) and stir at 40° C. for 6 days and then collect the solid by filter centrifugation (2 minutes, 5000 rpm, 0.22 μm PTFE membrane) to give the title compound.

Example 28

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.6 mg) is combined with 3:1 (v/v) ethanol/water having a water activity of about 0.7 (0.9 mL) and stir at 40° C. for 6 days and then collect the solid by filter centrifugation (2 minutes, 5000 rpm, 0.22 μm PVDF membrane) to give the title compound.

Example 29

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (69.7 mg) is combined with 1-propanol (10.8 mL) and heated to 60° C. while stirring. Dimethylsulfoxide (2 mL) was slowly added to about an 85:15 (v/v) mixture of 1-propanol/DMSO. The temperature was held at 60° C. for about 1.5 hours and then the mixture was cooled at a rate of 0.05° C./minute to 10° C. and held at 10° C. for 7.5 hours then 1-propanol (5 mL) was added and then the mixture was stirred at 5° C. for 10 days to give a solid which was collected by filtration to give the title compound.

Example 30

2-(3-(4-(7H-pyrrolo[2,3-d]pyrimidin-4-yl)-1H-pyrazol-1-yl)-1-(cyclopropylsulfonyl)azetidin-3-yl)acetonitrile Form III 2-(3-(4-(7H-pyrrolo[2,3-d]pyrimidin-4-yl)-1H-pyrazol-1-yl)-1-(cyclopropylsulfonyl)azetidin-3-yl)acetonitrile (70.6 mg) is combined with ethyl acetate saturated with water (0.2 mL) and heated to 60° C. while stirring and then added ethyl acetate (7.2 mL) and stirred at 60° C. for about 1.5 hours and then the mixture was cooled at a rate of 0.05° C./minute to 10° C. and then collect the solid by filter centrifugation (2 minutes, 5000 rpm, 0.2 PTFE membrane) to give the title compound.

Example 31

2-(3-(4-(7H-pyrrolo[2,3-d]pyrimidin-4-yl)-1H-pyrazol-1-yl)-1-(cyclopropylsulfonyl)azetidin-3-yl)acetonitrile Form III 2-(3-(4-(7H-pyrrolo[2,3-d]pyrimidin-4-yl)-1H-pyrazol-1-yl)-1-(cyclopropylsulfonyl)azetidin-3-yl)acetonitrile (199.6 mg) is combined with ethyl acetate saturated with water (2.0 mL) and stirred at room temperature for 2 days and then collect the solid by filter centrifugation (2 minutes, 5000 rpm, 0.2 μm PTFE membrane) to give the title compound.

Example 32

2-(3-(4-(7H-pyrrolo[2,3-d]pyrimidin-4-yl)-1H-pyrazol-1-yl)-1-(cyclopropylsulfonyl)azetidin-3-yl)acetonitrile Form I 2-(3-(4-(7H-pyrrolo[2,3-d]pyrimidin-4-yl)-1H-pyrazol-1-yl)-1-(cyclopropylsulfonyl)azetidin-3-yl)acetonitrile form III obtained from the material of Example 31 by drying under vacuum at 60° C. for about 69 hours to give the title compound.

Example 33

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.3 mg) is combined with ethanol (1 mL) and stir at 5° C. for 7 days and then collect the solid by filter centrifugation (2 minutes, 5000 rpm, 0.45 μm PVDF membrane) to give the title compound.

Example 34

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.4 mg) is combined with methanol (1 mL) and stir at 5° C. for 7 days and then collect the solid by filter centrifugation (2 minutes, 5000 rpm, 0.45 µm PVDF membrane) to give the title compound.

Example 35

2-(3-(4-(7H-pyrrolo[2,3-d]pyrimidin-4-yl)-1H-pyrazol-1-yl)-1-(cyclopropylsulfonyl)azetidin yl)acetonitrile Form II 2-(3-(4-(7H-pyrrolo[2,3-d]pyrimidin-4-yl)-1H-pyrazol-1-yl) (cyclopropylsulfonyl)azetidin-3-yl)acetonitrile (60.0 mg) is combined with isopropanol (1 mL) and stir at 5° C. for 7 days and then collect the solid by filter centrifugation (2 minutes, 5000 rpm, 0.45 µm PVDF membrane) to give the title compound.

Example 36

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.3 mg) is combined with 1-butanol (2 mL) and stir at 5° C. for 7 days and then collect the solid by filter centrifugation (2 minutes, 5000 rpm, 0.45 µm PVDF membrane) to give the title compound.

Example 37

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (59.6 mg) is combined with ethanol (1 mL) and stir at 60° C. for 5 days and then collect the solid by filter centrifugation (2 minutes, 5000 rpm, 0.45 µm PVDF membrane) to give the title compound.

Example 38

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (59.9 mg) is combined with methanol (1 mL) and stir at 60° C. for 5 days and then collect the solid by filter centrifugation (2 minutes, 5000 rpm, 0.45 µm PVDF membrane) to give the title compound.

Example 39

2-(3-(4-(7H-pyrrolo[2,3-d]pyrimidin-4-yl)-1H-pyrazol-1-yl)-1-(cyclopropylsulfonyl)azetidin yl)acetonitrile Form II 2-(3-(4-(7H-pyrrolo[2,3-d]pyrimidin-4-yl)-1H-pyrazol-1-yl) (cyclopropylsulfonyl)azetidin-3-yl)acetonitrile (60.1 mg) is combined with isopropanol (1.5 mL) and stir at 60° C. for 5 days and then collect the solid by filter centrifugation (2 minutes, 5000 rpm, 0.45 µm PVDF membrane) to give the title compound.

Example 40

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (60.6 mg) is combined with 1-butanol (1.5 mL) and stir at 60° C. for 5 days and then collect the solid by filter centrifugation (2 minutes, 5000 rpm, 0.45 µm PVDF membrane) to give the title compound.

Example 41

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (10.4 mg) is combined with acetonitrile (0.5 mL) and stir at 20° C. for 1 days and then collect the solid by filter centrifugation (1 minutes, 4500 g rcf, 0.2 µm PTFE membrane) to give the title compound.

Example 42

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (10.3 mg) is combined with acetone (0.5 mL) and stir at 20° C. for 1 days and then collect the solid by filter centrifugation (2 minutes, 4000 g rcf, 0.2 µm PTFE membrane) to give the title compound.

Example 43

2-(3-(4-(7H-pyrrolo[2,3-d]pyrimidin-4-yl)-1H-pyrazol-1-yl)-1-(cyclopropylsulfonyl)azetidin yl)acetonitrile Form II 2-(3-(4-(7H-pyrrolo[2,3-d]pyrimidin-4-yl)-1H-pyrazol-1-yl) (cyclopropylsulfonyl)azetidin-3-yl)acetonitrile (20.6 mg) is combined with 4:1 (v/v) methanol/water having a water activity of about 0.5 (0.4 mL) and stir at 25° C. for 4 days, then added additional 4:1 (v/v) methanol/water (0.5 mL) and stir at 25° C. for 6 days and then collect the solid by filter centrifugation (3 minutes, 5000 rpm, 0.2 µm PVDF membrane) to give the title compound.

Example 44

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (539.9 mg) is combined with 1:1 (v/v) ethanol/acetone (18 mL) and stir at 60° C. for 45 minutes and then cooled at a rate of 0.05° C./minute to a temperature of 5° C. to give a solid which was collected by filtration and dried under vacuum at 40° C. to give the title compound.

Example 45

2-(3-(4-(7H-pyrrolo[2,3-d]pyrimidin-4-yl)-1H-pyrazol-1-yl)-1-(cyclopropylsulfonyl)azetidin-3-yl)acetonitrile Form II 2-(3-(4-(7H-pyrrolo[2,3-d]pyrimidin-4-yl)-1H-pyrazol-1-yl)-1-(cyclopropylsulfonyl)azetidin-3-yl)acetonitrile (256.1 mg) is combined with 7:3 (v/v) acetone/isopropyl acetate (13.5 mL) and stir at 60° C. for 1 hour and then cooled at a rate of 0.02° C./minute to a temperature of 5° C. to give a solid which was collected by filtration and dried under vacuum at 40° C. to give the title compound.

Example 46

2-(3-(4-(7H-pyrrolo[2,3-d]pyrimidin-4-yl)-1H-pyrazol-1-yl)-1-(cyclopropylsulfonyl)azetidin-3-yl)acetonitrile Form III 2-(3-(4-(7H-pyrrolo[2,3-d]pyrimidin-4-yl)-1H-pyrazol-1-yl)-1-(cyclopropylsulfonyl)azetidin-3-yl)acetonitrile (60 mg) is combined with 5:1 (v/v) 1-butanol/water having a water activity of about 0.9 (2 mL) and stir at room temperature for 10 days and then collect the solid by filter centrifugation (2 minutes, 5000 rpm, 0.2 µm PTFE membrane) to give the title compound.

Example 47

2-(3-(4-(7H-pyrrolo[2,3-d]pyrimidin-4-yl)-1H-pyrazol-1-yl)-1-(cyclopropylsulfonyl)azetidin yl)acetonitrile Form III 2-(3-(4-(7H-pyrrolo[2,3-d]pyrimidin-4-yl)-1H-pyrazol-1-yl)-1-(cyclopropylsulfonyl)azetidin-3-yl)acetonitrile (60.1 mg) is combined with 1:1 (v/v) acetonitrile/water having a water activity of about 0.9 (0.9 mL) and stir at 40° C. for 6 days and then collect the solid by filter centrifugation (2 minutes, 5000 rpm, 0.2 µm PTFE membrane) to give the title compound.

Example 48

Control of Pruritus and Skin Lesions Associated with Allergic Dermatitis in Dogs This study evaluated 2-(3-(4-(7H-pyrrolo[2,3-d]pyrimidin-4-yl)-1H-pyrazol-1-yl)-1-(cyclopropylsulfonyl)azetidin-3-yl)acetonitrile for control of pruritus and skin lesions associated with allergic dermatitis in dogs.

Oral tablets were prepared containing Form II 2-(3-(4-(7H-pyrrolo[2,3-d]pyrimidin-4-yl)-1H-pyrazol-1-yl)-1-(cyclopropylsulfonyl)azetidin-3-yl)acetonitrile, as follows. Oral tablet blends were prepared containing crystal Form II 2-(3-(4-(7H-pyrrolo[2,3-d]pyrimidin-4-yl)-1H-pyrazol-1-yl)-1-(cyclopropylsulfonyl)azetidin-3-yl)acetonitrile, microcrystalline cellulose, pregelantinized starch, dicalcium phosphate dehydrate, oxide pigment, and magnesium stearate. The tablet blends were pressed giving tablet cores containing 2.4 mg, 3.6 mg, 5.4 mg, and 16 mg of crystal Form II 2-(3-(4-(7H-pyrrolo[2,3-d]pyrimidin-4-yl)-1H-pyrazol-1-yl)-1-(cyclopropylsulfonyl)azetidin-3-yl)acetonitrile, as well as a placebo core. The tablet cores were coated with a mixture containing water and Opadry 20A150011 Red, thereby giving the final oral tablets for the study.

TABLE 1

Tablet Blends

| Ingredient | Quantity (% w/w) | Placebo Quantity (% w/w) |
|---|---|---|
| 2-(3-(4-(7H-pyrrolo[2,3-d]pyrimidin-4-yl)-1H-pyrazol-1-yl)-1-(cyclopropylsulfonyl)azetidin-3-yl)acetonitrile | 2.4 | |
| Microcrystalline cellulose (Vivapur 302) | 52.0 | 52.0 |
| Pregelantinized starch (Starch 1500) | 12.0 | 12.0 |
| Dicalcium phosphate dehydrate (Di Tab) | 32.4 | 34.8 |
| Oxide pigment PB-150021 RED | 0.2 | 0.2 |
| Magnesium Stearate (Hyqual) | 1.0 | 1.0 |

A four-arm, blinded, randomized, placebo-controlled study was conducted to assess the efficacy of daily administration of 2-(3-(4-(7H-pyrrolo[2,3-d]pyrimidin-4-yl)-1H-pyrazol-1-yl)-1-(cyclopropylsulfonyl)azetidin-3-yl)acetonitrile for control of pruritus and skin lesions associated with allergic dermatitis in dogs. Subjects were randomized to one of the following treatment arms: API-containing Tablets, 0.25-0.40 mg/kg Body Weight; API-containing Tablets, 0.40-0.60 mg/kg Body Weight; API-containing Tablets, 0.60-0.80 mg/kg Body Weight; and Placebo Tablets, 0.0 mg/kg Body Weight.

Dogs enrolled in the study received once daily treatment for approximately 28 days. Baseline data (clinical history, concomitant therapies, body weight, physical examinations and assessments of pruritus and atopic dermatitis) were collected for each dog at enrollment (Day 0). Additional health assessments, physical examinations, body weight measurements, assessments of pruritus and atopic dermatitis, and collection of blood samples for hematology, serum chemistry and pharmacokinetic (PK) analysis occurred consistent with standard testing protocols.

The primary effectiveness variable was treatment success. A treatment success was defined as a 2 unit or more reduction from baseline on the 10-unit owner-assessed pruritus Visual-Analog Scale (VAS) in at least 70% of the first 7 treatment days (i.e., in at least 5 of the first 7 treatment days). Dogs withdrawn from the study within the first 7 days of treatment due to a perceived lack of effectiveness were considered treatment failures. The minimum effective dose was defined in the protocol as the dose at which treatment success is achieved in at least 50% of the dogs.

Table 2 shows that the highest dose of 2-(3-(4-(7H-pyrrolo[2,3-d]pyrimidin-4-yl)-1H-pyrazol-1-yl)-1-(cyclopropylsulfonyl)azetidin-3-yl)acetonitrile (0.60-0.80 mg/kg) had a response rate of 0.7188 (95% confidence interval 0.5331, 0.8512) which is statistically significantly higher than the placebo response rate of 0.2935 (0.1571, 0.4808); p-value for the comparison (on the log it scale) is 0.0006. Thus, the highest dose group (0.6-0.8 mg/kg) achieved the primary endpoint for treatment success. Furthermore, once daily dosing with 0.6-0.8 mg/kg showed significant improvements in pruritus from first dose, and the group showed a significant improvement in lesion scores at day 28 in the study. The estimated marginal mean response rate for low (0.24-0.4 mg/kg) and medium dose (0.4-0.6 mg/kg) were also higher than the placebo rate. This result is based on a generalized linear mixed model with fixed effect terms for treatment and Day 0 VAS score. Random effects were fit for site and site treatment with a variance component covariance structure and a compound symmetry covariance structure was fit for individual dogs.

TABLE 2

Treatment Success Generalized Linear Mixed Model Summary

| Treatment group | Number of dogs | LSMean | Std Err | 95% Confidence Limits | p-value vs placebo |
|---|---|---|---|---|---|
| 0.25-0.40 mg/kg | 43 | 0.4640 | 0.0919 | (0.2900, 0.6472) | 0.1336 |
| 0.40-0.60 mg/kg | 42 | 0.5590 | 0.0891 | (0.3772, 0.7261) | 0.0227 |
| 0.60-0.80 mg/kg | 42 | 0.7188 | 0.0809 | (0.5331, 0.8512) | 0.0006 |
| Placebo 0.0 mg/kg | 42 | 0.2935 | 0.0824 | (0.1571, 0.4808) | |

8. Exemplary Embodiments

For reasons of completeness, various aspects of the disclosure are set out in the following numbered clauses.

Clause 1. A substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising a peak at 12.72° (43.1%), 14.04° (61.3%), 17.56° (20.8%), 20.33° (87.4%), 24.50° (100%), and 25.83° (94.9%) (±0.2° 2θ).

Clause 2. A pharmaceutical composition comprising the substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of Clause 1, and a pharmaceutically acceptable excipient.

Clause 3. A process for making the substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of Clause 1, comprising crystallizing from acetone and heptane.

Clause 4. A process for making the substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of Clause 1, comprising drying a hydrated crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile.

Clause 5. A method of treating a dermatological condition comprising administering to a non-human mammal in need thereof an effective amount of the substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of Clause 1.

Clause 6. The method of Clause 5, wherein the dermatological condition is selected from the group consisting of atopic dermatitis and pruritus.

Clause 7. The method of Clause 6, wherein the non-human mammal is a dog.

Clause 8. A substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising a peak at 5.34°, 10.68°, 14.26°, 16.06°, 16.39°, 16.48°, 18.26°, 18.65°, 21.05°, 21.76°, 22.68°, or 26.75° (±0.2° 2θ).

Clause 9. A substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 18.65° and 10.68° (±0.2° 2θ).

Clause 10. A substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 18.65° and 21.76° (±0.2° 2θ).

Clause 11. A substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 18.65° and 22.68° (±0.2° 2θ).

Clause 12. A substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 26.75° and 21.76° (±0.2° 2θ).

Clause 13. A pharmaceutical composition comprising a substantially polymorphically pure crystalline 2-(3-(4-(7H-pyrrolo[2,3-d]pyrimidin-4-yl)-1H-pyrazol-1-yl) (cyclopropylsulfonyl)azetidin-3-yl)acetonitrile of any one of Clauses 8-12, and a pharmaceutically acceptable excipient.

Clause 14. A process for making a substantially polymorphically pure crystalline 2-(3-(4-(7H-pyrrolo[2,3-d]pyrimidin-4-yl)-1H-pyrazol-1-yl) (cyclopropylsulfonyl)azetidin-3-yl)acetonitrile of any one of Clauses 8-12, comprising crystallizing from a solvent or a mixture of solvents selected from the group consisting of $C_{1-5}$ alcohol, $C_{2-8}$ alkyl ether, $C_{2-8}$ alkyl acetate, $C_{2-5}$ alkyl cyanide, $C_{3-9}$ alkyl ketone, and aromatic solvent; each having a water activity of less than about 0.7.

Clause 15. A process for making a substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of any one of Clauses 8-12, comprising crystallizing from a solvent or a mixture of solvents selected from the group consisting of $C_{1-5}$ alcohol, $C_{2-8}$ alkyl ether, $C_{2-8}$ alkyl acetate, $C_{2-5}$ alkyl cyanide, $C_{3-9}$ alkyl ketone, and aromatic solvent; each having a water activity of less than about 0.5.

Clause 16. A process of making a substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of any one of Clauses 8-12, comprising crystallizing from acetonitrile having a water activity of less than 0.7.

Clause 17. A process of making a substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of any one of Clauses 8-12, comprising crystallizing from acetonitrile having a water activity of less than 0.5.

Clause 18. A method of treating a dermatological condition comprising administering to a non-human mammal in need thereof an effective amount of the crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of any one of Clauses 8-12.

Clause 19. The method of Clause 18, wherein the dermatological condition is selected from the group consisting of atopic dermatitis and pruritus.

Clause 20. The method of Clause 19, wherein the non-human mammal is a dog.

Clause 21. A substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising a peak at 11.08°, 14.73°, 18.06°, 18.27°, 18.51°, 22.24°, 22.69°, 24.76°, 25.48°, or 28.04° (±0.2° 2θ).

Clause 22. A substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 11.08° and 22.69° (±0.2° 2θ).

Clause 23. A substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 14.73° and 22.69° (±0.2° 2θ).

Clause 24. A substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 22.69° and 25.48° (±0.2° 2θ).

Clause 25. A substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 11.08° and 18.06° (±0.2° 2θ).

Clause 26. A substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 11.08° and 25.48° (±0.2° 2θ).

Clause 27. A pharmaceutical composition comprising a substantially polymorphically pure crystalline 2-(3-(4-(7H-pyrrolo[2,3-d]pyrimidin-4-yl)-1H-pyrazol-1-yl) (cyclopropylsulfonyl)azetidin-3-yl)acetonitrile of any one of Clauses 21-26, and a pharmaceutically acceptable excipient.

Clause 28. A process for making substantially polymorphically pure crystalline 2-(3-(4-(7H-pyrrolo[2,3-d]pyrimidin-4-yl)-1H-pyrazol-1-yl) (cyclopropylsulfonyl)azetidin-3-yl)acetonitrile of any one of Clauses 21-26, comprising crystallizing from a solvent or a mixture of solvents selected from the group consisting of $C_{1-5}$ alcohol, $C_{2-8}$ alkyl ether, $C_{2-8}$ alkyl acetate, $C_{2-5}$ alkyl cyanide, and $C_{3-9}$ alkyl ketone; each having a water activity of greater than about 0.9.

Clause 29. A process for making substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of any one of Clauses 21-26, comprising crystallizing from a solvent or a mixture of solvents selected from the group consisting of $C_{1-5}$ alcohol having a water activity of greater than about 0.9.

Clause 30. A method of treating a dermatological condition comprising administering to a non-human mammal in need thereof an effective amount of the crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of any one of Clauses 21-26.

Clause 31. The method of Clause 30, wherein the dermatological condition is selected from the group consisting of atopic dermatitis and pruritus.

Clause 32. The method of Clause 31, wherein the non-human mammal is a dog.

Clause 33. A substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising a peak at 5.34°, 10.68°, 14.26°, 16.06°, 16.39°, 16.48°, 18.26°, 18.65°, 21.05°, 21.76°, 22.68°, or 26.75° (±0.2° 2θ).

Clause 34. The substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of clause 33, characterized by the X-ray powder diffraction pattern comprising peaks at 18.65° and 10.68° (±0.2° 2θ).

Clause 35. The substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of clause 33, characterized by the X-ray powder diffraction pattern comprising peaks at 18.65° and 21.76° (±0.2° 2θ).

Clause 36. The substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of clause 33, characterized by the X-ray powder diffraction pattern comprising peaks at 18.65° and 22.68° (±0.2° 2θ).

Clause 37. The substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of clause 33, characterized by the X-ray powder diffraction pattern comprising peaks at 26.75° and 21.76° (±0.2° 2θ).

Clause 38. A pharmaceutical composition comprising a substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of any one of clauses 33 to 37, and a pharmaceutically acceptable excipient.

Clause 39. A process for making substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of any one of clauses 33 to 37, comprising crystallizing from a solvent or a mixture of solvents selected from the group consisting of $C_{1-5}$ alcohol, $C_{2-8}$ alkyl ether, $C_{2-8}$ alkyl acetate, $C_{2-5}$ alkyl cyanide, $C_{3-9}$ alkyl ketone, and aromatic solvent; each having a water activity of less than about 0.7.

Clause 40. A process for making substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of any one of clauses 33 to 37, comprising crystallizing from a solvent or a mixture of solvents selected from the group consisting of $C_{1-5}$ alcohol, $C_{2-8}$ alkyl ether, $C_{2-8}$ alkyl acetate, $C_{2-5}$ alkyl cyanide, $C_{3-9}$ alkyl ketone, and aromatic solvent; each having a water activity of less than about 0.5.

Clause 41. A process of making substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of any one of clauses 33 to 37, comprising crystallizing from acetonitrile having a water activity of less than 0.7.

Clause 42. A process of making substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile of any one of clauses 33 to 37, comprising crystallizing from acetonitrile having a water activity of less than 0.5.

Clause 43. A method of treating a dermatological condition, comprising administering to a non-human mammal in need thereof an effective amount of 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof.

Clause 44. A method of control of pruritus associated with allergic dermatitis and control of atopic dermatitis, comprising administering to a non-human mammal in need thereof an effective amount of 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof.

Clause 45. A method of treatment of pruritus associated with allergic dermatitis, comprising administering to a non-human mammal in need thereof an effective amount of 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof.

Clause 46. A method of treatment of clinical manifestations of atopic dermatitis, comprising administering to a non-human mammal in need thereof an effective amount of 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof.

Clause 47. The method of any one of clauses 43-46, wherein the non-human mammal is dog.

Clause 48. The method of clause 47, wherein the dog is at least 12 months of age.

Clause 49. The method of any one of clauses 43-48, wherein the effective amount is 0.6-0.8 mg/kg.

Clause 50. The method of any one of clauses 43-49, wherein administration to the non-human mammal is once daily.

Clause 51. The method of any one of clauses 43-50, wherein the 2-(3-(4-(7H-pyrrolo[2,3-d]pyrimidin-4-yl)-1H-pyrazol-1-yl)-1-(cyclopropylsulfonyl)azetidin-3-yl)acetonitrile is crystalline.

Clause 52. The method of any one of clauses 43-51, wherein the 2-(3-(4-(7H-pyrrolo[2,3-d]pyrimidin-4-yl)-1H-pyrazol-1-yl)-1-(cyclopropylsulfonyl)azetidin-3-yl)acetonitrile is crystalline Form I, crystalline Form II, crystalline Form III, or any combination thereof.

Clause 53. The method of any one of clauses 43-51, wherein the 2-(3-(4-(7H-pyrrolo[2,3-d]pyrimidin-4-yl)-1H-pyrazol-1-yl)-1-(cyclopropylsulfonyl)azetidin-3-yl)acetonitrile is a substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising a peak at 5.34°, 10.68°, 14.26°, 16.06°, 16.39°, 16.48°, 18.26°, 18.65°, 21.05°, 21.76°, 22.68°, or 26.75° (±0.2° 2θ).

Clause 54. The method of any one of clauses 43-51, wherein the 2-(3-(4-(7H-pyrrolo[2,3-d]pyrimidin-4-yl)-1H-pyrazol-1-yl)-1-(cyclopropylsulfonyl)azetidin-3-yl)acetonitrile is a substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 18.65° and 10.68° (±0.2° 2θ).

Clause 55. The method of any one of clauses 43-51, wherein the 2-(3-(4-(7H-pyrrolo[2,3-d]pyrimidin-4-yl)-1H-pyrazol-1-yl)-1-(cyclopropylsulfonyl)azetidin-3-yl)acetonitrile is a substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 18.65° and 21.76° (±0.2° 2θ).

Clause 56. The method of any one of clauses 43-51, wherein the 2-(3-(4-(7H-pyrrolo[2,3-d]pyrimidin-4-yl)-1H-pyrazol-1-yl)-1-(cyclopropylsulfonyl)azetidin yl)acetonitrile is a substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 18.65° and 22.68° (±0.2° 2θ).

Clause 57. The method of any one of clauses 43-51, wherein the 2-(3-(4-(7H-pyrrolo[2,3-d]pyrimidin-4-yl)-1H-pyrazol-1-yl)-1-(cyclopropylsulfonyl)azetidin-3-yl)acetonitrile is a substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising peaks at 26.75° and 21.76° (±0.2° 2θ).

Clause 58. An oral dosage form comprising 2-(3-(4-(7H-pyrrolo[2,3-d]pyrimidin-4-yl)-1H-pyrazol-1-yl)-1-(cyclopropylsulfonyl)azetidin-3-yl)acetonitrile or a salt thereof.

Clause 59. An oral dosage form comprising 2-(3-(4-(7H-pyrrolo[2,3-d]pyrimidin-4-yl)-1H-pyrazol-1-yl)-1-(cyclopropylsulfonyl)azetidin-3-yl)acetonitrile.

Clause 60. An oral dosage form comprising crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile.

Clause 61. An oral dosage form comprising 2.4 mg, 3.6 mg, 4.8 mg, 5.4 mg, 6.4 mg, 8.5 mg, 15 mg, or 16 mg of 2-(3-(4-(7H-pyrrolo[2,3-d]pyrimidin-4-yl)-1H-pyrazol-1-yl)-1-(cyclopropylsulfonyl)azetidin-3-yl)acetonitrile.

Clause 62. The oral dosage form of any one of clauses 58-61, wherein the 2-(3-(4-(7H-pyrrolo[2,3-d]pyrimidin-4-yl)-1H-pyrazol-1-yl)-1-(cyclopropylsulfonyl)azetidin-3-yl)acetonitrile is Form I, Form II, or Form III of 2-(3-(4-(7H-pyrrolo[2,3-d]pyrimidin-4-yl)-1H-pyrazol-1-yl)-1-(cyclopropylsulfonyl)azetidin-3-yl)acetonitrile, or a combination thereof.

Clause 63. The oral dosage form of any one of clauses 58-62, wherein the 2-(3-(4-(7H-pyrrolo[2,3-d]pyrimidin-4-yl)-1H-pyrazol-1-yl)-1-(cyclopropylsulfonyl)azetidin-3-yl)acetonitrile is substantially polymorphically pure crystalline 2-(3-(4-(7H-pyrrolo[2,3-d]pyrimidin-4-yl)-1H-pyrazol-1-yl)-1-(cyclopropylsulfonyl)azetidin-3-yl)acetonitrile characterized by the X-ray powder diffraction pattern comprising a peak at 5.34°, 10.68°, 14.26°, 16.06°, 16.39°, 16.48°, 18.26°, 18.65°, 21.05°, 21.76°, 22.68°, or 26.75° (±0.2° 2θ).

Clause 64. The oral dosage form of any one of clauses 58-63, wherein the oral dosage form further comprises microcrystalline cellulose, pregelantinized starch, dicalcium phosphate dehydrate, oxide pigment, or magnesium stearate, or any combination thereof.

The invention claimed is:
1. A crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile of formula (I):

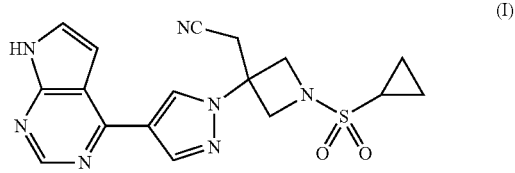 [SMILES: N#CCC1(n2cc(-c3ncnc4[nH]ccc34)cn2)CN(S(=O)(=O)C2CC2)C1]

wherein the crystalline form is Form II;
wherein crystalline Form II of 2-(3-(4-(7H-pyrrolo[2,3-d]pyrimidin-4-yl)-1H-pyrazol-1-yl)-1-(cyclopropylsulfonyl)azetidin-3-yl)acetonitrile is characterized by a X-ray powder diffraction pattern comprising at least one characteristic peak (° 2θ) at 5.34°±0.2° 2θ, 10.68°±0.2° 2θ, 14.26°±0.2° 2θ, 16.06°±0.2° 2θ, 16.39°±0.2° 2θ, 16.48°±0.2° 2θ, 18.26°±0.2° 2θ, 18.65°±0.2° 2θ, 21.05°±0.2° 2θ, 21.76°±0.2° 2θ, 22.68°±0.2° 2θ, or 26.75°±0.2° 2θ; and wherein the X-ray powder diffraction pattern is determined on a diffractometer using CuKα radiation.

2. The crystalline form of claim 1, wherein the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile is characterized by a X-ray powder diffraction pattern comprising characteristic peaks (° 2θ) at 10.68°±0.2° 2θ and 18.65°±0.2° 2θ.

3. The crystalline form of claim 1, wherein the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile is characterized by a X-ray powder diffraction pattern comprising characteristic peaks (° 2θ) at 18.65°±0.2° 2θ and 21.76°±0.2° 2θ.

4. The crystalline form of claim 1, wherein the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile is characterized by a X-ray powder diffraction pattern comprising characteristic peaks (° 2θ) at 18.65°±0.2° 2θ and 22.68°±0.2° 2θ.

5. The crystalline form of claim 1, wherein the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile is characterized by a X-ray powder diffraction pattern comprising characteristic peaks (° 2θ) at 21.76°±0.2° 2θ and 26.75°±0.2° 2θ.

6. The crystalline form of claim 1, wherein the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile is characterized by a X-ray powder diffraction pattern comprising characteristic peaks (° 2θ) at 5.34°±0.2° 2θ, 10.68°±0.2° 2θ, 14.26°±0.2° 2θ, 16.06°±0.2° 2θ, 16.39°±0.2° 2θ, 16.48°±0.2° 2θ, 18.26°±0.2° 2θ, 18.65°±0.2° 2θ, 21.05°±0.2° 2θ, 21.76°±0.2° 2θ, 22.68°±0.2° 2θ, and 26.75°±0.2° 2θ.

7. The crystalline form of claim 1, wherein the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile has a polymorphic purity of greater than 90%.

8. The crystalline form of claim 1, wherein the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile has a polymorphic purity of greater than 97%.

9. The crystalline form of claim 1, wherein the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile has a polymorphic purity of greater than 99%.

10. The crystalline form of claim 1, wherein the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile has a polymorphic purity of greater than 99.5%.

11. A pharmaceutical composition comprising a pharmaceutically acceptable excipient and the crystalline form of claim 1.

12. A method for treating a dermatological condition in a non-human mammal, wherein the method comprises administering to the non-human mammal in need thereof a therapeutically effective amount of a crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile of formula (I):

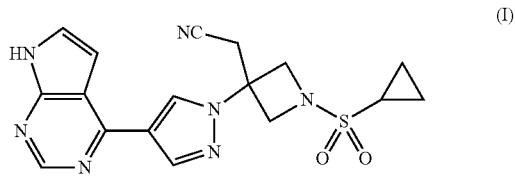 [SMILES: N#CCC1(n2cc(-c3ncnc4[nH]ccc34)cn2)CN(S(=O)(=O)C2CC2)C1]

wherein the crystalline form is Form II;
wherein crystalline Form II of 2-(3-(4-(7H-pyrrolo[2,3-d]pyrimidin-4-yl)-1H-pyrazol-1-yl)-1-(cyclopropylsulfonyl)azetidin-3-yl)acetonitrile is characterized by a X-ray powder diffraction pattern comprising at least one characteristic peak (° 2θ) at 5.34°±0.2° 2θ, 10.68°±0.2° 2θ, 14.26°±0.2° 2θ, 16.06°±0.2° 2θ, 16.39°±0.2° 2θ, 16.48°±0.2° 2θ, 18.26°±0.2° 2θ, 18.65°±0.2° 2θ, 21.05°±0.2° 2θ, 21.76°±0.2° 2θ, 22.68°±0.2° 2θ, or 26.75°±0.2° 2θ; and
wherein the X-ray powder diffraction pattern is determined on a diffractometer using CuKα radiation.

13. The method of claim 12, wherein the dermatological condition is a skin disorder selected from the group consisting of atopic dermatitis, pruritis, psoriasis, a skin irritation, a skin rash, and a skin sensitization, or a combination thereof.

14. The method of claim 13, wherein the dermatological condition is atopic dermatitis.

15. The method of claim 13, wherein the dermatological condition is pruritis.

16. The method of claim 13, wherein the non-human mammal is a dog.

17. The method of claim 16, wherein the dog is at least 9 months of age.

18. The method of claim 16, wherein the dog is at least 12 months of age.

19. The method of claim 12, wherein the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile is characterized by a X-ray powder diffraction pattern comprising characteristic peaks (° 2θ) at 10.68°±0.2° 2θ and 18.65°±0.2° 2θ.

20. The method of claim 12, wherein the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile is characterized by a X-ray powder diffraction pattern comprising characteristic peaks (° 2θ) at 18.65°±0.2° 2θ and 21.76°±0.2° 2θ.

21. The method of claim 12, wherein the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile is characterized by a X-ray powder diffraction pattern comprising characteristic peaks (° 2θ) at 18.65°±0.2° 2θ and 22.68°±0.2° 2θ.

22. The method of claim 12, wherein the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile is characterized by a X-ray powder diffraction pattern comprising characteristic peaks (° 2θ) at 21.76°±0.2° 2θ and 26.75°±0.2° 2θ.

23. The method of claim 12, wherein the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile is characterized by a X-ray powder diffraction pattern comprising characteristic peaks (° 2θ) at 5.34°±0.2° 2θ, 10.68°±0.2° 2θ, 14.26°±0.2° 2θ, 16.06°±0.2° 2θ, 16.39°±0.2° 2θ, 16.48°±0.2° 2θ, 18.26°±0.2° 2θ, 18.65°±0.2° 2θ, 21.05°±0.2° 2θ, 21.76°±0.2° 2θ, 22.68°±0.2° 2θ, and 26.75°±0.2° 2θ.

24. The method of claim 23, wherein:
(a) the non-human mammal is a dog; and
(b) the dermatological condition is atopic dermatitis.

25. The method of claim 12, wherein the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile has a polymorphic purity of greater than 90%.

26. The method of claim 12, wherein the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile has a polymorphic purity of greater than 97%.

27. The method of claim 12, wherein the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile has a polymorphic purity of greater than 99%.

28. The method of claim 12, wherein the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile has a polymorphic purity of greater than 99.5%.

29. The method of claim 12, wherein the method further comprises administering to the non-human mammal in need thereof a therapeutically effective amount of the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile of formula (I) in the range of 0.1 mg/kg to 1.2 mg/kg.

30. The method of claim 12, wherein the method further comprises administering daily to the non-human mammal in need thereof a therapeutically effective amount of the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile of formula (I).

31. The method of claim 12, wherein the method further comprises administering twice daily to the non-human mammal in need thereof a therapeutically effective amount of the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile of formula (I).

32. The method of claim 12, wherein the method further comprises administering weekly to the non-human mammal in need thereof a therapeutically effective amount of the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile of formula (I).

33. The method of claim 12, wherein the method further comprises administering monthly to the non-human mammal in need thereof a therapeutically effective amount of the crystalline form of 2-(3-(4-(7H-pyrrolo[2,3-d]pyrimidin-4-yl)-1H-pyrazol-1-yl)-1-(cyclopropylsulfonyl)azetidin-3-yl)acetonitrile of formula (I).

* * * * *